United States Patent
Lu et al.

(10) Patent No.: US 10,487,114 B2
(45) Date of Patent: *Nov. 26, 2019

(54) METHODS FOR ADMINISTERING PEPTIDES FOR THE GENERATION OF EFFECTIVE C/S CONFORMATION-SPECIFIC ANTIBODIES TO A HUMAN SUBJECT IN NEED THEREOF

(75) Inventors: Kun Ping Lu, Newton, MA (US); Xiao Zhen Zhou, Newton, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/113,991

(22) PCT Filed: Apr. 27, 2012

(86) PCT No.: PCT/US2012/035473
§ 371 (c)(1),
(2), (4) Date: Apr. 8, 2014

(87) PCT Pub. No.: WO2012/149334
PCT Pub. Date: Nov. 1, 2012

(65) Prior Publication Data
US 2014/0242100 A1    Aug. 28, 2014

Related U.S. Application Data

(60) Provisional application No. 61/479,665, filed on Apr. 27, 2011.

(51) Int. Cl.
*A61K 38/06* (2006.01)
*A61K 38/08* (2019.01)
(Continued)

(52) U.S. Cl.
CPC ............ *C07K 7/08* (2013.01); *A61K 39/0007* (2013.01); *C07K 16/18* (2013.01); *C07K 16/44* (2013.01);
(Continued)

(58) Field of Classification Search
None
See application file for complete search history.

(56) References Cited

U.S. PATENT DOCUMENTS 4,489,078 A    12/1984   Temple, Jr.
4,591,588 A    5/1986    Wade
(Continued)

FOREIGN PATENT DOCUMENTS

WO    WO-83/00229 A1    1/1983
WO    WO-9607399 A1     3/1996
(Continued)

OTHER PUBLICATIONS

Citron, Alzheimer's disease: strategies for disease modification. Naturee Reviews | Drug Discovery vol. 9 | May 2010 | 387-398.*
(Continued)

*Primary Examiner* — Aurora M Fontainhas
(74) *Attorney, Agent, or Firm* — Clark & Elbing LLP

(57) ABSTRACT

The present invention features methods and compositions for the generation of conformation-specific antibodies.

12 Claims, 4 Drawing Sheets

Specification includes a Sequence Listing.

(51) Int. Cl.

| | | |
|---|---|---|
| *C07K 7/00* | (2006.01) | |
| *C07K 14/40* | (2006.01) | |
| *C07K 14/47* | (2006.01) | |
| *C07K 7/08* | (2006.01) | |
| *A61K 39/00* | (2006.01) | |
| *C07K 16/18* | (2006.01) | |
| *C07K 16/44* | (2006.01) | |

(52) U.S. Cl.
CPC ......... *C07K 2317/33* (2013.01); *Y02A 50/466* (2018.01)

(56) References Cited

U.S. PATENT DOCUMENTS

| | | |
|---|---|---|
| 4,734,413 A | 3/1988 | Wade |
| 4,816,567 A | 3/1989 | Cabilly et al. |
| 5,530,101 A | 6/1996 | Queen et al. |
| 5,627,153 A | 5/1997 | Little, II et al. |
| 5,639,600 A | 6/1997 | McGrath et al. |
| 5,654,010 A | 8/1997 | Johnson et al. |
| 5,821,337 A | 10/1998 | Carter et al. |
| 5,952,467 A | 9/1999 | Hunter et al. |
| 5,972,697 A | 10/1999 | Hunter et al. |
| 6,054,297 A | 4/2000 | Carter et al. |
| 6,093,550 A | 7/2000 | Chang et al. |
| 6,165,464 A | 12/2000 | Hudziak et al. |
| 6,299,863 B1 | 10/2001 | Aberg et al. |
| 6,365,157 B2 | 4/2002 | Rockwell et al. |
| 6,462,173 B1 | 10/2002 | Lu et al. |
| 6,495,376 B1 | 12/2002 | Lu et al. |
| 6,555,583 B2 | 4/2003 | Nieman et al. |
| 6,562,363 B1 | 5/2003 | Mantelle et al. |
| 6,569,839 B1 | 5/2003 | McKay |
| 6,596,848 B1 | 7/2003 | Hunter et al. |
| 6,696,248 B1 | 2/2004 | Knappik et al. |
| 6,706,484 B1 | 3/2004 | Knappik et al. |
| 6,828,422 B1 | 12/2004 | Achim et al. |
| 6,830,745 B1 | 12/2004 | Budny et al. |
| 6,864,275 B1 | 3/2005 | Camden et al. |
| 6,869,974 B1 | 3/2005 | Del Soldato |
| 6,894,033 B2 | 5/2005 | Cruz et al. |
| 6,984,654 B2 | 1/2006 | Camden |
| 7,056,917 B2 | 6/2006 | Nakayama et al. |
| 7,087,648 B1 | 8/2006 | McGrath |
| 7,112,578 B2 | 9/2006 | Levin |
| 7,125,677 B2 | 10/2006 | Hunter et al. |
| 7,125,842 B2 | 10/2006 | Kawabe et al. |
| 7,125,955 B2 | 10/2006 | Hunter et al. |
| 7,148,003 B2 | 12/2006 | Hunter et al. |
| 7,161,060 B1 | 1/2007 | Duff et al. |
| 7,164,012 B2 | 1/2007 | Hunter et al. |
| 7,199,119 B2 | 4/2007 | Burkitt et al. |
| 7,202,259 B2 | 4/2007 | Chen |
| 7,217,737 B2 | 5/2007 | Chen et al. |
| 7,264,963 B1 | 9/2007 | Knappik et al. |
| 8,129,131 B2 | 3/2012 | Lu et al. |
| 8,258,099 B2 | 9/2012 | Lu et al. |
| 2002/0025521 A1 | 2/2002 | Lu et al. |
| 2002/0168684 A1 | 11/2002 | Comb et al. |
| 2004/0171019 A1 | 9/2004 | Matthews et al. |
| 2005/0221391 A1* | 10/2005 | Davies ............... 435/7.2 |
| 2005/0239095 A1 | 10/2005 | Lu et al. |
| 2006/0074222 A1 | 4/2006 | Lu et al. |
| 2006/0258564 A1* | 11/2006 | Pluschke et al. ......... 514/7 |
| 2007/0172496 A1 | 7/2007 | Olesen |
| 2008/0058276 A1 | 3/2008 | Lu et al. |
| 2008/0118505 A1 | 5/2008 | Tedder |
| 2008/0131438 A1 | 6/2008 | Barden et al. |
| 2008/0214470 A1 | 9/2008 | Lu et al. |
| 2008/0248043 A1 | 10/2008 | Babcook et al. |
| 2009/0258352 A1 | 10/2009 | Lu et al. |
| 2010/0278832 A1 | 11/2010 | Kamogawa et al. |
| 2011/0104756 A1 | 5/2011 | Rodriguez et al. |
| 2012/0183560 A1 | 7/2012 | Akassoglou |
| 2013/0028900 A1 | 1/2013 | Lu et al. |
| 2014/0086909 A1 | 3/2014 | Lu et al. |
| 2018/0072814 A1 | 3/2018 | Lu et al. |

FOREIGN PATENT DOCUMENTS

| | | |
|---|---|---|
| WO | WO-96/40072 A2 | 12/1996 |
| WO | WO-97/03692 A1 | 2/1997 |
| WO | WO-97/17986 A1 | 5/1997 |
| WO | WO-99/09969 A1 | 3/1999 |
| WO | WO-02/065091 A2 | 8/2002 |
| WO | WO-02/092765 A2 | 11/2002 |
| WO | WO-2004/016751 A2 | 2/2004 |
| WO | WO-2004/101745 A2 | 11/2004 |
| WO | WO-2005/027727 A2 | 3/2005 |
| WO | WO-2008/006087 A2 | 1/2008 |
| WO | WO-2009/146218 A2 | 12/2009 |
| WO | WO-2011/056561 A1 | 5/2011 |
| WO | WO-2012/162698 A1 | 11/2012 |
| WO | WO-2013/185055 A1 | 12/2013 |
| WO | WO-2014/152157 A2 | 9/2014 |

OTHER PUBLICATIONS

Tabira, Immunization therapy for Alzheimer disease: a comprehensive review of active immunization strategies.Tohoku J Exp Med. Feb. 2010;220(2):95-106. (Year: 2010).*

Ma et al., "Antibody catalysis of peptidyl-prolyl cis-trans isomerization in the folding of RNase T1," Proc Natl Acad Sci USA. 95(13):7251-6 (1998).

International Search Report for International Application No. PCT/US2012/035473, dated Dec. 10, 2012 (5 pages).

Written Opinion of the International Search Authority for International Application No. PCT/US2012/035473, dated Dec. 10, 2012 (7 pages).

U.S. Appl. No. 61/968,862, Lu et al.

Asuni et al., "Immunotherapy targeting pathological tau conformers in a tangle mouse model reduces brain pathology with associated functional improvements," J Neurosci. 27(34):9115-29 (2007).

Boimel et al., "Efficacy and safety of immunization with phosphorylated tau against neurofibrillary tangles in mice," Exp Neurol. 224(2):472-85 (2010).

Boutajangout et al., "Immunotherapy targeting pathological tau prevents cognitive decline in a new tangle mouse model," J Neurosci. 30(49):16559-66 (2010).

Esnault et al., "Pin1 modulates the type 1 immune response," PLoS One. 2(2):e226 (2007).

International Search Report and Written Opinion for International Application No. PCT/US14/027017, dated Oct. 28, 2014 (19 pages).

International Search Report for International Application No. PCT/US2012/039850, dated Oct. 3, 2012 (3 pages).

Jeong et al., "Novel role of Pin1 induction in type II collagen-mediated rheumatoid arthritis," J Immunol. 183(10):6689-97 (2009).

Kayed et al., "Prefilament tau species as potential targets for immunotherapy for Alzheimer disease and related disorders," Curr Opin Immunol. 21(3):359-63 (2009).

Nakamura, et al. "Proline isomer-specific antibodies reveal the early pathogenic tau conformation in Alzheimer's disease" Cell. 149(1):232-44 (2012).

Ubhi et al., "Recent advances in the development of immunotherapies for tauopathies," Exp Neurol. 230(2):157-61 (2011).

Wisniewski et al., "Vaccination as a therapeutic approach to Alzheimer's disease," Mt Sinai J Med. 77(1):17-31 (2010).

Written Opinion of the International Searching Authority for International Application No. PCT/US2012/039850, dated Oct. 3, 2012 (5 pages).

Bayry et al., "Intravenous immunoglobulin for infectious diseases: back to the pre-antibiotic and passive prophylaxis era?," Trends Pharmacol Sci. 25(6):306-10 (2004).

Campbell, General properties and applications of monoclonal antibodies. *Monoclonal Antibody Technology: The Production and Characterization of Rodent and Human Hybridomas.* Elsevier Science, 1-32 (1984).

(56) References Cited

OTHER PUBLICATIONS

Casadevall et al., "Passive antibody therapy for infectious diseases," Nat Rev Microbiol. 2(9):695-703 (2004).
Clackson et al., "Making antibody fragments using phage display libraries," Nature. 352(6336):624-8 (1991).
Dunman et al., "Passive immunization as prophylaxis: when and where will this work?," Curr Opin Pharmacol. 3(5):486-96 (2003).
Enever et al., "Next generation immunotherapeutics—honing the magic bullet," Curr Opin Biotechnol. 20(4):405-11 (2009).
Huse et al., "Generation of a large combinatorial library of the immunoglobulin repertoire in phage lambda," Science. 246(4935):1275-81 (1989).
International Search Report for International Application No. PCT/US10/54077, dated Feb. 15, 2011 (5 pages).
Jicha et al., "A conformation- and phosphorylation-dependent antibody recognizing the paired helical filaments of Alzheimer's disease," J Neurochem. 69(5):2087-95 (1997).
Jones et al., "Replacing the complementarity-determining regions in a human antibody with those from a mouse," Nature. 321(6069):522-5 (1986).
Köhler et al., "Continuous cultures of fused cells secreting antibody of predefined specificity," Nature. 256(5517):495-7 (1975).
Köhler et al., "Derivation of specific antibody-producing tissue culture and tumor lines by cell fusion," Eur J Immunol. 6(7): 511-519 (1976).
Lim et al., "Pinning down phosphorylated tau and tauopathies," Biochim Biophys Acta. 1739(2-3):311-322 (2005).
Lu et al., "Pinning down proline-directed phosphorylation signaling," Trends Cell Biol. 12(4):164-72 (2002).
Lu et al., "Prolyl cis-trans isomerization as a molecular timer," Nat Chem Biol. 3(10):619-629 (2007) (11 pages).
Lu et al., "Targeting carcinogenesis: a role for the prolyl isomerase Pin1?," Mol Carcinog. 45(6):397-402 (2006).
Lu et al., "The prolyl isomerase PIN1: a pivotal new twist in phosphorylation signalling and disease," Nat Rev Mol Cell Biol. 8(11):904-16 (2007).
Lu, KP. "Pinning down cell signaling, cancer and Alzheimer's disease," Trends Biochem Sci. 29(4):200-9 (2004).
Lummis et al., "Cis-trans isomerization at a proline opens the pore of a neurotransmitter-gated ion channel," Nature. 438(7065):248-52 (2005).
Marks et al., "By-passing immunization. Human antibodies from V-gene libraries displayed on phage," J Mol Biol. 222(3):581-97 (1991).
Pastorino et al., "Phosphorylation of the amyloid precursor protein (APP): is this a mechanism in favor or against Alzheimer's disease," Neurosci Res Commun. 35(3):213-31 (2004).
Presta, "Antibody engineering," Curr Opin Struct Biol. 2:593-596 (1992).
Riechmann et al., "Reshaping human antibodies for therapy," Nature. 332(6162):323-7 (1988).
Wang et al., "Serine-cis-proline and serine-trans-proline isosteres: stereoselective synthesis of (Z)- and (E)-alkene mimics by Still-Wittig and Ireland-Claisen rearrangements," J Org Chem. 68(6):2343-9 (2003).
Wulf et al., "Phosphorylation-specific prolyl isomerization: is there an underlying theme?," Nat Cell Biol. 7(5):435-41 (2005).
An et al., "Retention of the cis proline conformation in tripeptide fragments of bovine pancreatic ribonuclease A containing a non-natural proline analogue, 5,5-dimethylproline," J Am Chem Soc. 121(49):11558-66 (1999).
Harlow et al., Immunizations. *Antibodies: a Laboratory Manual.* Cold Spring Harbor Laboratory Press, 76 (1988).
Office Action for U.S. Appl. No. 14/325,013, dated Sep. 2, 2015 (45 pages).
Wittelsberger et al., "Pseudoprolines: Targeting a cis Conformation in a Mimetic of the gp120 V3 Loop of HIV-1," Angew Chem Int Ed Engl. 39(6):1111-5 (2000).
Lemere, "Immunotherapy for Alzheimer's disease: hoops and hurdles," Mol Neurodegener. 8:36 (2013) (6 pages).

\* cited by examiner

US 10,487,114 B2

METHODS FOR ADMINISTERING PEPTIDES FOR THE GENERATION OF EFFECTIVE C/S CONFORMATION-SPECIFIC ANTIBODIES TO A HUMAN SUBJECT IN NEED THEREOF

CROSS-REFERENCE TO RELATED APPLICATIONS

This application is the U.S. National Stage filing under 35 U.S.C. § 371 of International Application No. PCT/US2012/035473, filed Apr. 27, 2012, which claims benefit of U.S. Provisional Application No. 61/479,665, filed Apr. 27, 2011.

STATEMENT AS TO FEDERALLY SPONSORED RESEARCH

This invention was made with government support under grants GM058556 and AG017870 awarded by NIH. The government has certain rights in the invention.

BACKGROUND OF THE INVENTION

In general, the invention relates to methods and compositions for the generation and use of conformation-specific antibodies or fragments thereof.

Protein phosphorylation is a key cellular signaling mechanism that induces changes in protein conformation. For example, the phosphorylation of specific serine or threonine residues that immediately precede a proline residue (Ser/Thr-Pro motif) is a central regulatory mechanism in the cell. The unique stereochemistry of the proline residue means that the peptidyl-prolyl bond of the Ser/Thr-Pro motif can adopt two different conformational states (i.e., a cis conformation or a trans conformation). Peptidyl-prolyl cis/trans isomerases (PPIases) specifically catalyze the cis/trans isomerization of Ser/Thr-Pro motifs and, thus, regulate the structure of these proteins between the two distinct conformations.

Pin1 is a unique PPIase that specifically catalyzes the cis/trans isomerization of certain phosphorylated Ser/Thr-Pro (pSer/Thr-Pro) motifs. The identification of Pin1 as a phosphorylation-specific PPIase led to the understanding of a new signaling mechanism, whereby Pin1 catalytically regulates the conformation of its substrates after their phosphorylation to further control protein function. Indeed, Pin1-catalyzed conformational changes control many protein functions. Moreover, Pin1 is tightly regulated by multiple mechanisms, and the deregulation of Pin1 plays a pivotal role in some human diseases (e.g., cancer, Alzheimer's disease, and asthma). Given the completely different conformation of cis and trans Ser/Thr-Pro motifs (e.g., phosphorylated and nonphosphorylated Ser/Thr-Pro motifs), the use of conformation specific antigenic peptides would allow for treatment of disorders associated with specific protein conformations.

Thus, there exists a need in the art for conformation-specific antibodies that specifically bind to a cis or trans conformation of a Xaa-Pro (e.g., Ser/Thr-Pro or phosphorylated Ser/Thr-Pro) motif of a polypeptide, where Xaa may be any amino acid residue.

SUMMARY OF THE INVENTION

In one aspect, the invention features a method of generating a conformation-specific antibody that specifically binds to a Xaa-Pro motif (e.g., fixed in the cis or trans conformation) of a polypeptide (e.g., a PPIase substrate or, more specifically, a Pin1 substrate), where Xaa is any amino acid residue (e.g., wherein Xaa is serine, threonine, phosphorylated, and/or not phorphorylated), the method including administering (e.g., subcutaneously administering) a proline-analog-containing antigenic peptide to a human subject in an amount sufficient to generate the conformation-specific antibody, the antigenic peptide including a Xaa-Pro motif (e.g., fixed in the cis or trans conformation). The antibody can, e.g., bind to the cis conformation of the Xaa-Pro motif of the polypeptide with at least 10- to 100-fold greater affinity than to the trans conformation of the Xaa-Pro motif of the polypeptide, or bind to the trans conformation of the Xaa-Pro motif of the polypeptide with at least 10- to 100-fold greater affinity than to the cis conformation of the Xaa-Pro motif of the polypeptide. This method may further include the administration of a booster dose and the antigenic peptide can be further formulated with an immunostimulating adjuvant In another aspect, the invention features a method of treating a human subject with a disorder (e.g., a disorder associated with a deregulation of PPIase activity). This method includes:
(i) contacting a sample from the subject with a conformation-specific antibody or fragment thereof that specifically binds to a Xaa-Pro motif of a polypeptide present in the sample, where the peptidyl-prolyl bond of the Xaa-Pro motif is in a cis conformation and wherein the Xaa is any amino acid residue;
(ii) quantitating the amount of the conformation-specific antibody or fragment thereof bound to the Xaa-Pro motif in the cis conformation; and
(iii) comparing the amount of the Xaa-Pro motif in the cis conformation in the sample to the amount of the Xaa-Pro motif in the cis conformation found in subjects diagnosed with the disorder or subjects not diagnosed with the disorder,
(iv) administering a proline-analog-containing antigenic peptide to the subject if an increase in the amount of the Xaa-Pro motif in the cis conformation in the subject, in comparison to the amount of the Xaa-Pro motif in the cis conformation in the subjects not diagnosed with the disorder, is determined.

In this method, administering the proline-analog-containing antigenic peptide to the subject treats the disorder. This method can further include monitoring the Xaa-Pro motif in the cis conformation in the subject after the administration of the proline-analog-containing antigenic peptide.

In another aspect, the invention features a method of treating a human subject with a disorder (e.g., a disorder associated with a deregulation of PPIase activity). This method includes:
(i) contacting a sample from the subject with a conformation-specific antibody or fragment thereof that specifically binds to a Xaa-Pro motif of a polypeptide present in the sample, where the peptidyl-prolyl bond of the Xaa-Pro motif is in a trans conformation and wherein the Xaa is any amino acid residue;
(ii) quantitating the amount of the conformation-specific antibody or fragment thereof bound to the Xaa-Pro motif in the trans conformation; and
(iii) comparing the amount of the Xaa-Pro motif in the trans conformation in the sample to the amount of the Xaa-Pro motif in the trans conformation found in subjects diagnosed with the disorder or subjects not diagnosed with the disorder, (iv) administering a proline-analog-containing antigenic peptide to the subject if an increase in the amount of the Xaa-Pro motif in the trans conformation in the subject, in comparison to the amount of the Xaa-Pro motif in the trans conformation in the subjects not diagnosed with the disorder, is determined.

In this method, administering the proline-analog-containing antigenic peptide to the subject treats the disorder. This method can further include monitoring the Xaa-Pro motif in the trans conformation in the subject after the administration of the proline-analog-containing antigenic peptide.

In any of the foregoing methods, the Pin1 substrate can be any of the substrates listed in Tables 1, 2A-2C, or 3. For example, the Pin1 substrate can be NIMA, RAB4, CDC25, WEE1, PLK1, MYT1, CDC27, CENP-F, Incenp, RBP1, NHERF-1, KRMP1, CK2, TopoIIα, DAB2, p54nrb, Sil, EMI1, cyclin D1, Ki67, c-Myc, cyclin E, c-Jun, β-catenin, Cf-2, NF-κB, RAF1, C-Fos, RARα, AIB1/SRC-3, HBx, STAT3, p53, Bcl-2, p73, BimEL, p66$^{Shc}$, CHE1, tau, amyloid precursor protein (APP), APP fragment, synphilin-1, gephyrin, MCL1, NFAT, AUF1, IRF3, BTK, SIN3-RPD3, or hSpt5.

Also, in any of the foregoing methods, the proline analog can be homoproline, pipecolic acid (PIP), dimethyl proline (DMP), azetidine-2-carboxylic acid (Aze), tert-butyl-L-proline (TBP), trans-4-fluoro-L-proline (t-4F-Pro), 2,2-dimethyl-thiazolidine (Thz), or cis-4-fluoro-L-proline (c-4F-Pro).

In any of the foregoing methods, the subject can have, or be at risk of developing, a tauopathy (e.g., Alzheimer's disease, frontotemproal dementia with Parkinsonism liked to chromosome 17, Pick's disease, and a corticobasal degeneration), a cell proliferation disorder (e.g., cancer, benign prostatic hyperplasia, psoriasis, abnormal keratinization, lymphoproliferative disorders, rheumatoid arthritis, arteriosclerosis, restenosis, diabetic retinopathy, retrolental fibrioplasia, neovascular glaucoma, angiofibromas, hemangiomas, Karposi's sarcoma, and neurodegenerative disorders), and/or a neurological disorder (Alzheimer's disease, mild cognitive impairment, Parkinson's disease, multiple sclerosis, muscular dystrophy, corticobasal degeneration, dementia pugilistica, Down's syndrome, frontotemporal dementias, myotonic dystrophy, Niemann-Pick disease, Pick's disease, prion disease, progressive supranuclear palsy, subacute sclerosing panencephalistis, convulsive disorders, vascular dementia, age-related dementia, head trauma, stroke, neurofibromatosis, Lewy body disease, amyotrophic lateral sclerosis, peripheral neuropathies, and macular degeneration).

In one aspect, normal subjects can be administered a proline-analog-containing antigenic peptide in an amount sufficient to generate the conformation specific antibody that in turn may function prophylactically to reduce the risk of developing a tauopathy.

The above antigenic peptides can be at least 8 amino acid residues in length (e.g., between 8 and 20 amino acid residues in length). For example, the antigenic peptide can a peptide including the sequence KVAVVR-(pT231)-(Dmp)-PKSPS (SEQ ID NO: 1) or the sequence KKVA-VVR-(pT231)-(Thz)-PKSPS (SEQ ID NO: 2).

As used herein, the term "abnormal cell growth" is intended to include cell growth that is undesirable or inappropriate. Abnormal cell growth also includes proliferation that is undesirable or inappropriate (e.g., unregulated cell proliferation or undesirably rapid cell proliferation). Abnormal cell growth can be benign and result in benign masses of tissue or cells (e.g., benign tumors). Many art-recognized conditions are associated with such benign masses or benign tumors, including, for example, diabetic retinopathy, retrolental fibrioplasia, neovascular glaucoma, psoriasis, angiofibromas, rheumatoid arthritis, hemangiomas, and Karposi's sarcoma. Abnormal cell growth can also be malignant and result in malignancies, malignant masses of tissue or cells, or malignant tumors. Many art-recognized conditions and disorders are associated with malignancies, malignant masses, and malignant tumors, including, for example, cancer and carcinoma.

By "adjuvant" is meant one or more substances that cause stimulation of the immune system. In this context, an adjuvant is used to enhance an immune response to one or more vaccine antigens or antibodies. An adjuvant may be administered to a subject before, in combination with, or after administration of the vaccine. Examples of chemical compounds used as adjuvants include, but are not limited to, aluminum compounds, oils, block polymers, immune stimulating complexes, vitamins and minerals (e.g., vitamin E, vitamin A, selenium, and vitamin B 12), Quil A (saponins), bacterial and fungal cell wall components (e.g., lipopolysaccharides, lipoproteins, and glycoproteins), hormones, cytokines, and co-stimulatory factors.

By "antibody" is meant monoclonal antibodies, polyclonal antibodies, humanized antibodies, chimeric antibodies, recombinant antibodies, multispecific antibodies, and antibody fragments. The antibody may be, for example, a conformation-specific antibody (e.g., an antibody that binds to the cis or trans conformation of a Xaa-Pro motif). An antibody specifically binds to an antigen. The antibody may also be a non-immunoglobulin binding polypeptide.

By "antigen" is meant a molecule to which an antibody can selectively bind. The target antigen may be a protein (e.g., an antigenic peptide), carbohydrate, nucleic acid, lipid, hapten, or other naturally occurring or synthetic compound. The target antigen may be a polypeptide (e.g., a polypeptide containing a Xaa-Pro motif (e.g., a phosphorylated or non-phosphorylated Ser/Thr-Pro motif)) or peptide mimics (e.g., a polypeptide containing a Xaa-homoproline motif, Xaa-5, 5-dimethylproline motif (Dmp), and Xaa-2,2-dimethyl-thiazolidine (Thz)). An antigen may also be administered to an animal to generate an immune response in the animal.

By "binding affinity" is meant the strength of the total noncovalent interactions between a single binding site of a molecule (e.g., an antibody) and its binding partner (e.g., an antigen or antigenic peptide). Unless otherwise indicated, as used herein, "binding affinity" refers to intrinsic binding affinity, which reflects a specific interaction between members of a binding pair (e.g., antibody and antigen). The affinity of a molecule X for its partner Y can generally be represented by the dissociation constant ($K_d$). Affinity can be measured by standard methods known in the art, including those described herein. A low-affinity complex contains an antibody that generally tends to dissociate readily from the antigen, whereas a high-affinity complex contains an antibody that generally tends to remain bound to the antigen for a longer duration.

By "cancer" and "cancerous" is meant the physiological condition in mammals that is typically characterized by abnormal cell growth. Included in this definition are benign and malignant cancers, as well as dormant tumors or micrometastases. Examples of cancer include, but are not limited to, carcinoma, lymphoma, blastoma, sarcoma, and leukemia. More particular examples of such cancers include, e.g., prostate cancer, squamous cell cancer, small-cell lung cancer, non-small-cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, vulval cancer, thyroid cancer, hepatic carcinoma, gastric cancer, melanoma, and various types of head and neck cancer.

By "cell proliferation disorder" is meant a disorder associated with abnormal cell growth. Exemplary cell proliferative disorders include cancer (e.g., benign and malignant), benign prostatic hyperplasia, psoriasis, abnormal keratinization, lymphoproliferative disorders, rheumatoid arthritis, arteriosclerosis, restenosis, diabetic retinopathy, retrolental fibrioplasia, neovascular glaucoma, angiofibromas, hemangiomas, Karposi's sarcoma, and neurodegenerative disorders. Cellular proliferative disorders are described, for example, in U.S. Pat. Nos. 5,639,600, 7,087,648, and 7,217,737, hereby incorporated by reference. By "conformation-specific antibody" is an antibody or fragment thereof that recognizes and specifically binds to a particular conformation (e.g., a conformational isomer or conformer) of its complementary antigen. For example, as described herein, the conformation-specific antibody may specifically bind to the cis conformation of a Xaa-Pro motif, but will not specifically bind to the trans conformation of the Xaa-Pro motif, where Xaa is any amino acid residue (e.g., serine or threonine). In this case, the conformation-specific antibody will have, for example, at least 10- to 100-fold greater affinity to the cis conformation than to the trans conformation of a Xaa-Pro motif. Conversely, the conformation-specific antibody may specifically bind to the trans conformation of a Xaa-Pro motif, but will not specifically bind to the cis conformation of the Xaa-Pro motif, where Xaa is any amino acid residue (e.g., serine or threonine). In certain embodiments, the Ser/Thr-Pro motif may be phosphorylated (i.e., pSer/Thr-Pro).

By "disorder" is meant any condition that may be treated, inhibited, diagnosed, or screened for according to the methods of the invention described herein. By "disorder associated with a deregulation of PPIase activity" is meant a disorder in which PPIase (e.g., Pin1) activity is modulated (e.g., upregulated or downregulated). Non-limiting examples of disorders associated with a deregulation of PPIase activity to be treated, inhibited, diagnosed, or screened for by the methods and compositions described herein include, e.g., cellular proliferation disorders (e.g., cancer), neurological disorders (e.g., Alzheimer's disease), aging-related disorders, asthma, and microbial infections.

By "neurological disorder" is meant a disturbance in the structure or function of the nervous system resulting from a developmental abnormality, disorder, injury, or toxin. Exemplary neurological disorders include Alzheimer's disease (AD), mild cognitive impairment (MCI), frontotemporal dementia with Parkinsonism linked to chromosome 17 (FTDP-17), Pick's disease, corticobasal degeneration and other tauopathies, Parkinson's disease (PD), multiple sclerosis (MS), muscular dystrophy, corticobasal degeneration, dementia pugilistica, Down's syndrome, frontotemporal dementias, myotonic dystrophy, Niemann-Pick disease, Pick's disease, prion disease, progressive supranuclear palsy, subacute sclerosing panencephalistis, convulsive disorders (e.g., epilepsy), vascular dementia, age-related dementia, head trauma, stroke, neurofibromatosis, Lewy body disease, amyotrophic lateral sclerosis (ALS), peripheral neuropathies, and macular degeneration.

By "pharmaceutically acceptable carrier" is meant a carrier that is physiologically acceptable to the treated subject while retaining the therapeutic properties of the composition (e.g., the antigenic peptide) with which it is administered. One exemplary pharmaceutically acceptable carrier substance is physiological saline. Other physiologically acceptable carriers and their formulations are known to one skilled in the art and are described, for example, in Remington's Pharmaceutical Sciences ($20^{th}$ edition, ed. A. Gennaro, 2000, Lippincott, Williams & Wilkins, Philadelphia, Pa.).

By "protein," "polypeptide," "polypeptide fragment," or "peptide" is meant any chain of more than two amino acid residues, regardless of post-translational modification (e.g., glycosylation or phosphorylation), constituting all or part of a naturally occurring polypeptide or peptide or constituting a non-naturally occurring polypeptide or peptide. A polypeptide or peptide may be said to be "isolated" or "substantially pure" when physical, mechanical, or chemical methods have been employed to remove the polypeptide from cellular constituents.

The peptides and polypeptides of the invention, as defined above, include all "mimetic" and "peptidomimetic" forms. The terms "mimetic" and "peptidomimetic" refer to a synthetic chemical compound that has substantially the same structural and/or functional characteristics of the peptides (e.g., antigenic peptides) or polypeptides of the invention. The mimetic can be either entirely composed of synthetic, non-natural analogs of amino acids or may be a chimeric molecule of natural amino acids and non-natural analogs of amino acids. The mimetic can also incorporate any amount of conservative substitutions, as long as such substitutions do not substantially alter the mimetic's structure or activity.

By "proline analog" is meant a molecule substantially similar in function to either an entire proline amino acid residue or to a fragment thereof. For example, the present invention contemplates the use of proline analogs wherein a side chain is lengthened or shortened while still providing a carboxyl, amino, or other reactive precursor functional group, as well as proline analogs having variant side chains with appropriate functional groups. Exemplary proline analogs include, without limitation, homoproline (i.e., pipecolic acid (PIP)), 5,5-dimethyl proline (DMP), azetidine-2-carboxylic acid (Aze), tert-butyl-L-proline (TBP), trans-4-fluoro-L-proline (t-4F-Pro), 2,2-dimethyl-thiazolidine (Thz), or cis-4-fluoro-L-proline (c-4F-Pro).

By "reduce or inhibit" is meant the ability to cause an overall decrease of 20% or greater, of 50% or greater, or of 75%, 80%, 85%, 90%, 95%, or greater. For therapeutic applications, to "reduce or inhibit" can refer to the symptoms of the disorder being treated or the presence or extent of a disorder being treated. For diagnostic or monitoring applications, to "reduce or inhibit" can refer to a decrease in the level of protein or nucleic acid detected by the diagnostic or monitoring assays.

By "reference" is meant any sample, standard, or level that is used for comparison purposes. A "normal reference sample" can be a prior sample taken from the same subject prior to the onset of a disorder (e.g., a cellular proliferation disorder or a neurological disorder), a sample from a subject not having the disorder, a subject that has been successfully treated for the disorder, or a sample of a purified reference polypeptide at a known normal concentration. By "reference standard or level" is meant a value or number derived from a reference sample. A normal reference standard or level can be a value or number derived from a normal subject that is matched to a sample of a subject by at least one of the following criteria: age, weight, disease stage, and overall health. In one example, a normal reference level of, for example, a polypeptide indicative of a disorder or a conformation of a polypeptide indicative of a disorder, is less than 5 ng/ml in a serum sample, less than 4 ng/ml, less than 3 ng/ml, less than 2 ng/ml, or less than 1 ng/ml in a serum sample. A "positive reference" sample, standard, or value is a sample, standard, value, or number derived from a subject that is known to have a disorder (e.g., a cellular proliferation disorder or a neurological disorder) that is matched to a sample of a subject by at least one of the following criteria: age, weight, disease stage, and overall health. For example, a positive reference value for, e.g., a polypeptide indicative of a disorder, is greater than 5 ng/ml serum, greater than 10 ng/ml serum, greater than 20 ng/ml, greater than 30 ng/ml, greater than 40 ng/ml, or greater than 50 ng/ml serum.

By "specifically binds" is meant a molecule (e.g., an antibody) which recognizes and binds another molecule (e.g., an antigen), but that does not substantially recognize and bind other molecules. In one example, an antibody that specifically binds the cis conformation of a Xaa-Pro motif of a polypeptide does not specifically bind the trans conformation of a Xaa-Pro motif of a polypeptide, where Xaa is any amino acid residue (e.g., serine or threonine). The term "specific binding," "specifically binds to," or is "specific for" a particular molecule (e.g., a polypeptide, an epitope on of a polypeptide, or a conformation of a polypeptide), as used herein, can be exhibited, for example, by a molecule having a $K_d$ for the molecule to which it binds of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, or greater.

The term "specifically binds" may also refer to binding where a molecule (e.g., an antibody) binds to a particular polypeptide (e.g., a polypeptide containing a Xaa-Pro motif, where Xaa is any amino acid residue (e.g., serine or threonine)), an epitope on a particular polypeptide, or a conformation of a particular polypeptide (e.g., a cis conformation of a Xaa-Pro motif) without substantially binding to any other polypeptide, polypeptide epitope, or polypeptide conformation (e.g., the trans conformation of a Xaa-Pro motif). For example, the conformation-specific antibody may have, for example, at least 10- to 100-fold greater affinity (e.g., $10^1$-, $10^2$-, $10^3$-, $10^4$-, $10^5$-, $10^6$-, $10^7$-, $10^8$-, $10^9$-, or $10^{10}$-fold greater affinity) to one conformation (e.g., the cis conformation) than to another conformation (e.g., the trans conformation) of, for example, a Ser/Thr-Pro motif. By "subject" is meant a mammal, including, but not limited to, a human or non-human mammal, such as a bovine, equine, canine, ovine, or feline.

By "treating" is meant administering a pharmaceutical composition for therapeutic purposes or administering treatment to a subject already suffering from a disorder to improve the subject's condition. By "treating a disorder" is meant that the disorder and the symptoms associated with the disorder are, e.g., alleviated, reduced, cured, or placed in a state of remission.

By "vaccine," as used herein, is meant a composition that elicits an immune response in a subject to which it is administered.

Other features and advantages of the invention will be apparent from the following detailed description, the drawings, and the claims.

DETAILED DESCRIPTION

Figure 1:
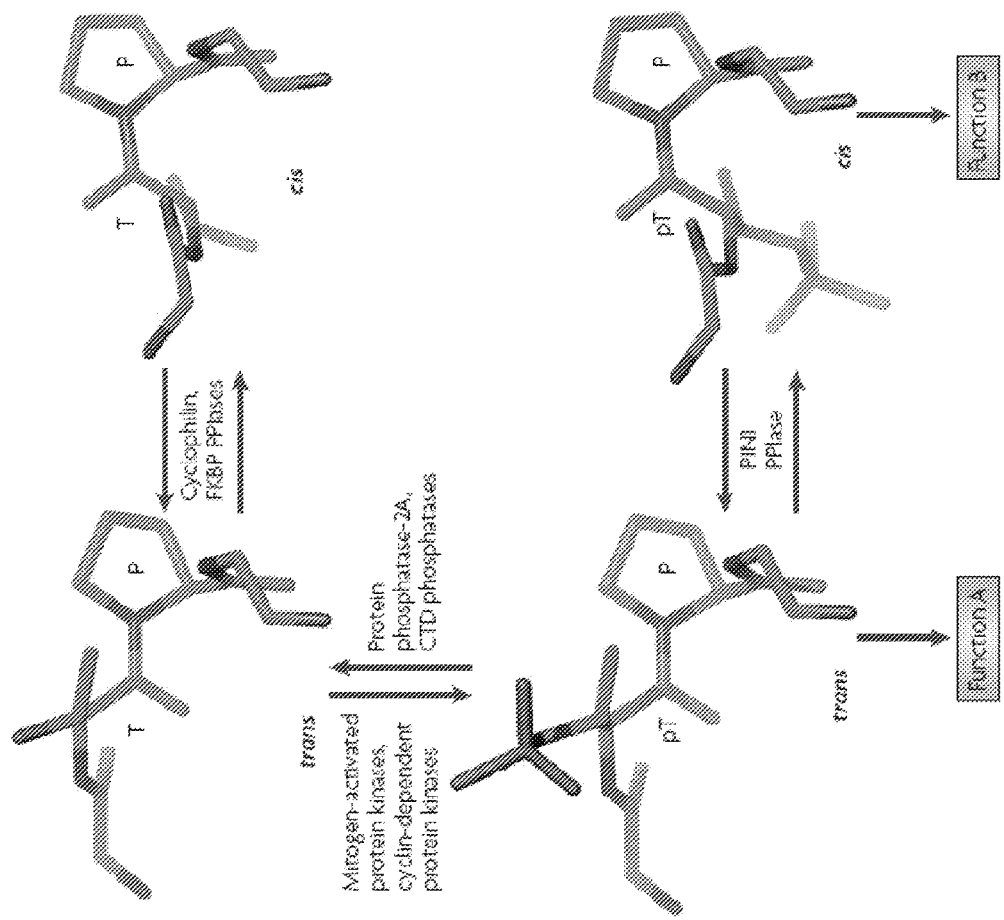
FIG. 1 is a schematic diagram showing the Pin1-catalyzed conformational switch between the cis and trans conformation of pSer/Thr-Pro motifs.
Figure 2:
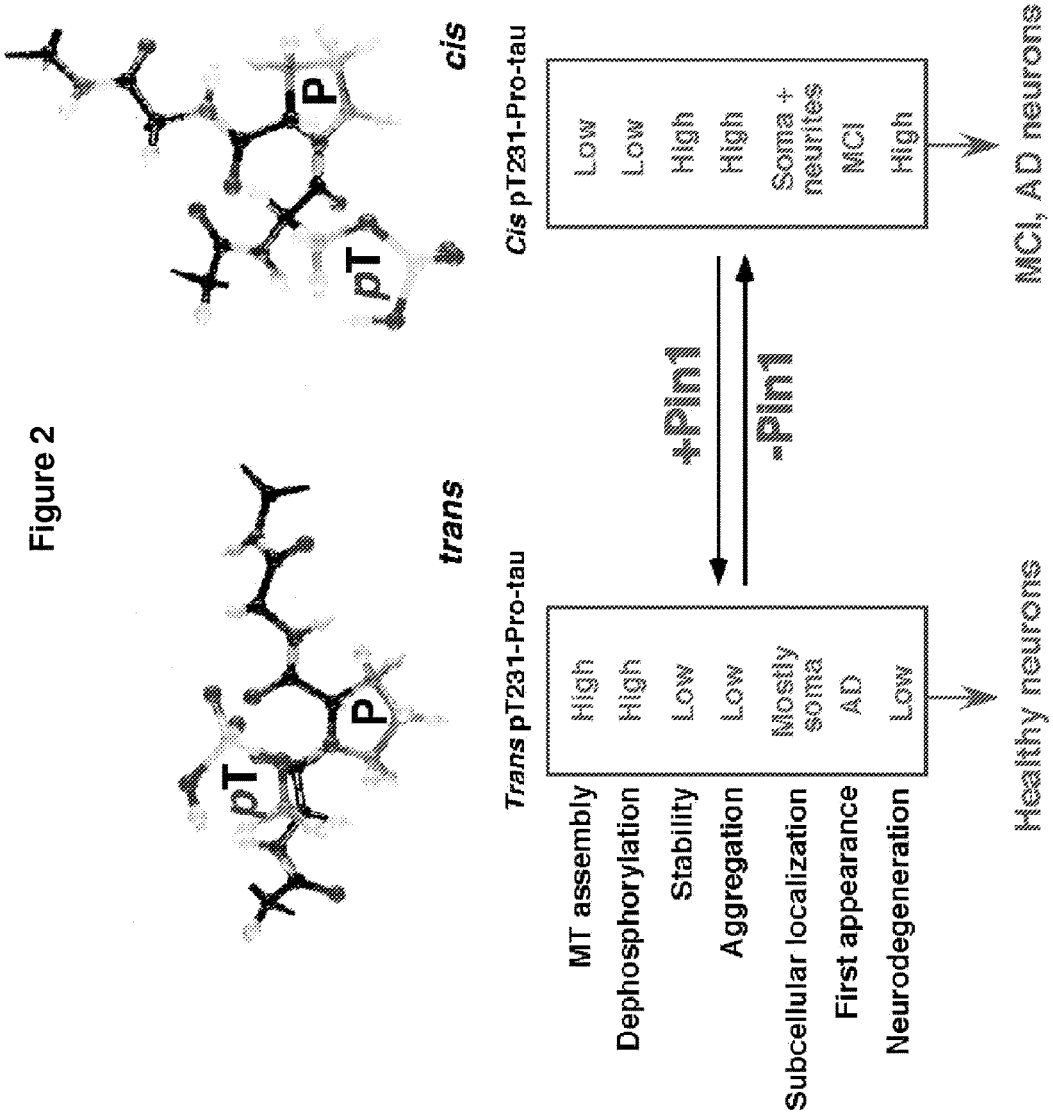
FIG. 2 is a schematic diagram showing that Pin1 prevents the accumulation of the pathological cis pThr231-tau conformation in AD by converting it to the nonpathological trans. pThr231-tau protein exists in the two completely distinct cis and trans conformations, as depicted in cartoons of the primary backbone structures. Cis, but not trans, pThr231-tau loses normal tau function and also gains toxic function. Cis, but not trans, pThr231-tau appears early in MCI neurons, accumulates only in degenerated neurons and localizes to dystrophic neurites in AD. Pin1 prevents the accumulation of the pathological cis pThr231-tau conformation in AD by converts it to the non-pathological trans conformation.

We describe the administration of antigenic peptides (e.g., as vaccines) to generate conformation specific antibodies in humans. In particular, we describe generation of antibodies specific to the cis or trans conformation of the phosphorylated Ser/Thr-Pro motif using antigenic formulations containing proline analogs (Nakamura et al Cell 149, 232-244, 2012, herein incorporated by reference in its entirety). These methods are useful for eliciting an immune response specific for either the cis or trans conformation of particular polypeptides, e.g., in order to treat or decrease the likelihood of certain disorders, including cancer, Alzheimer's disease, asthma, inflammation, immune diseases, and aging.

Vaccines and antibodies are the $1^{st}$ and $2^{nd}$ largest classes of human drugs used in clinics because they are not only highly effective and specific in attacking the intended target, but can be administrated long before disease develops, often with no or minimal side effects. Immunotherapy targeting Aβ peptides using vaccines and/or peripherally administered antibodies reduces Aβ burden and prevents memory loss in AD mouse models, but clinical trials have encountered difficulties or are still ongoing. It has recently been accepted that misfolded tau also is a valuable drug target for AD. Current tau-related therapeutic strategies include inhibiting the kinases, activating the phosphatases, stabilizing microtubules, facilitating misfolded tau degradation, and preventing or reversing tau aggregation. Development of immunotherapy against tau has fallen behind in part because misfolded tau was traditionally thought to be intracellular and thereby inaccessible to antibodies. However, immunization against some pS/T-P motifs including pT231-P, has been shown to reduce tau aggregates and improve memory deficits in mouse models (see, e.g., Asuni et al. J Neurosci 27, 9115-9129 (2007), Boutajangout et al. J Neurosci 30, 16559-16566 (2010), Boimel et al. Exp Neurol 224, 472-485 (2010), Kayed et al. Curr Opin Immunol 21, 359-363 (2009), Wisniewski et al. Mt Sinai J Med 77, 17-31 (2010), and Ubhi et al. Exp Neurol (2010), each of which is incorporated by reference its entirety). This outcome is supported by the findings that vaccination is effective in reducing intracellular α-synuclein aggregates in animal models and that Aβ antibodies can be internalized to clear intraneuronal Aβ aggregates in neurons. Furthermore, tau aggregates can be internalized to promote tau fibrillization in cell cultures and injection of fibrillary tau brain extracts into the brain of mice overexpressing wild-type human tau can induce the formation of human tau into filaments and the spread of tau pathology into neighboring brain regions. Thus, immunotherapy against p-tau is becoming an attractive new option for treating tauopathies. However, our new results suggest that it would be more effective and specific to target only the pathological conformation of Pro-directed phosphorylation sites.

Pathology of Cis/Trans Conformation of PPIase Substrates

Proline is an amino acid residue unique in its ability to adopt either the cis or trans conformation. Due to the relatively large energy barrier of its isomerization ($\epsilon^a$=14 to 24 kcal mol$^{-1}$), uncatalyzed isomerization is a slow process, but may be accelerated by PPIases (see, e.g., FIGS. 1 and 3). PPIases facilitate protein folding and include, for example, cyclophilins (Cyps), FK506-binding proteins (FKBPs), and parvulin-like PPIases (e.g. Pin1 and Ess1).

Pin1 (protein interacting with NIMA (never in mitosis A)-1) specifically isomerizes phosphorylated Ser/Thr-Pro (pSer/Thr-Pro) motifs of certain polypeptides, which is important because proline-directed kinases (e.g., protein kinases that phosphorylate certain Ser/Thr residues that precede a proline residue) and phosphatases are conformation-specific and generally act only on the trans conformation. Pin1 has a two-domain structure that includes an N-terminal WW domain and a C-terminal PPIase domain, and structure-function analyses have shown that the unique substrate specificity of Pin1 towards specific pSer/Thr-Pro motifs results from interactions provided by both the WW domain and the PPIase domain. The PPIase activity of Pin1 facilitates the regulation of, for example, growth-signal responses, cell-cycle progression, cellular stress responses, neuronal function, and immune responses.

Decreased Pin1 activity can result in pathologic accumulation of either the cis or trans conformation of a particular polypeptide depending on the relative stability of a particular conformation. For example, a decrease in Pin1 activity could result in a pathologic accumulation of the cis conformation of a protein if the cis conformation was more resistant to protein degradation. Antibodies specific to pathologic conformations of individual proteins can be useful in blocking (e.g., through inducing degradation or precipitation) of pathological conformations of protein.

As described below, compared with trans p-tau, the cis conformation is less able to promote microtubule assembly, and more resistant to dephosphorylation and degradation, and more prone to aggregation, indicating that cis, but not trans, p-tau both loses normal function and gains toxic function. Pin1 accelerates cis to trans conversion in wild-type p-tau in vitro and in vivo. Thus, during MCI and AD, cis p-tau is the pathological conformation but is converted to the less or non-toxic trans by Pin1. Antibodies specific to the cis p-tau can be used to deplete the neural tissue of the pathological conformation of the protein.

Exemplary substrates of Pin1, each containing motifs capable of being isomerized, are listed in Table 1. The functional consequences of isomerization of the substrates are also listed, Peptides containing locked conformations of any of Tables 1, 2A-2C, or 3 of Pin1 target sites are useful in generating conformation specific antibodies in humans. The invention includes antigenic peptides including one or more of each of the PIN1 substrate target sites.

TABLE 1

General Pin1 Substrates

| Substrate (GenBank Accession Number) | Targeting Site(s) | Functional Consequence of PPIase Activity of Pin1 Upon Substrate |
|---|---|---|
| G2/M and Mitotic Regulation | | |
| NIMA (P11837) | — | Regulation of mitotic function |
| RAB4 (NP_004569) | — | — |
| CDC25 (AAA58417) | pThr48/67-Pro | Dephosphorylation and regulation of activity |
| WEE1 (NP_003381) | pT186-P | Inhibition of WEE1 activity |
| PLK1 (P53350) | — | — |
| MYT1 (NP_004194) | — | — |
| CDC27 (AAH11656) | — | — |
| CENP-F (P49454) | — | — |
| Incenp (NP_064623) | — | — |
| RPB1 (CAA65619) | pSer5-Pro | Regulation of CTD dephosphorylation |
| NHERF-1 (AAA80218) | pSer279/301-P | Dephosphorylation |
| KRMP1 (NP_057279) | pT-1604-P | Regulation of mitotic function |
| CK2 (NP_808227) | Multiple pSer/Thr-Pro sites | Inhibition of kinase activity |
| TopoIIα (NP_001058) | — | Inhibition or induction of phosphorylation |
| DAB2 (NP_001334) | — | Dephosphorylation |
| p54nrb (CAA72157) | Multiple pSer/Thr-Pro sites | — |
| Sil (CAC14001) | Multiple pSer/Thr-Pro sites | Regulation of function |
| EMI1 (NP_036309) | pS10-P | Stabilization |
| G1/S Regulation | | |
| Cyclin D1 (NP_444284) | pT286-P | Stabilization and nuclear localization |
| Ki67 | pT234-P | — |
| c-Myc (CAA46984) | pT58-P | Dephosphorylation and destabilization |
| Cyclin E (P24864) | pS384-P | Destabilization |

TABLE 1-continued

General Pin1 Substrates

| Substrate (GenBank Accession Number) | Targeting Site(s) | Functional Consequence of PPIase Activity of Pin1 Upon Substrate |
|---|---|---|
| *Growth and Oncogenic Signaling* | | |
| c-Jun (AAH06175) | pS63/73-P | Transactivation |
| B-catenin (P35222) | pS246-P | Stabilization, protein interaction, and transactivation |
| Cf-2 (NP_034298) | — | Destabilization |
| NF-κB (AAH33210) | pT254-P | Stabilization, protein interaction, and transactivation |
| RAF1 (AAA60247) | Multiple pSer/Thr-Pro sites | Dephosphorylation and prolonging activation |
| c-Fos (CAA24756) | Multiple pSer/Thr-Pro sites | Transactivation |
| RARα (NP_001019980) | pS77-P | Stabilization and transactivation |
| AIB1/SRC-3 | — | Transactivation and destabilization |
| HBx (NP_110380) | pS41-P | Stabilization and potentiation |
| STAT3 (NP_998827) | pS727-P | Transactivation |
| *DNA Damage, Oxidative Stress Response, and Apoptosis* | | |
| p53 (BAC16799) | Multiple pSer/Thr-Pro sites | Stabilization and transactivation |
| Bcl-2 (NP_000648) | pS70/87-P | — |
| p73 (CAA72221) | Multiple pSer/Thr-Pro sites | Stabilization and transactivation |
| BimEL (AAC39593) | pS65-P | Stabilization |
| p66$^{Shc}$ (AAH14158) | — | Mitochondrial import |
| CHE1 (P06276) | — | Destabilization |
| *Neuronal Survival and Degeneration* | | |
| Tau (NP_058519) | pT231-P pT212-P | Dephosphorylation and protein interaction |
| APP (P05067) | pT668-P | Promotes non-amyloidogenic APP processing and reduces Aβ production |
| APP fragment | pT668-P | Increases Aβ production from C99 APP fragment |
| Synphilin-1 (AAD30362) | pS211/215-P | Protein interaction |
| Gephyrin (CAC81240) | pS188/194/200-P | Protein interaction |
| MCL1 (CAI15504) | pT163-P | Stabilization |
| *Immune Response and Asthma* | | |
| NFAT (NP_666017) | — | |
| AUF1 (NP_112738) | — | Protein interaction |
| IRF3 (AAH71721) | pS339-P | Destabilization |
| BTK (CAI42359) | pS21/115-P | Destabilization |
| *Others* | | |
| SIN2-RPD3 | — | Reduces histone deacetylases |
| hSpt5 (NP_001124297) | — | |

TABLE 2A

Pin1 targets where Pin1 prevents protein from degradation

| | PROTEIN NAME | PIN1 FUNCTION | PIN1 BINDING MOTIF | KINASE/ PHOSPHATASE | PATHWAYS/ DISEASES/ MECHANISM |
|---|---|---|---|---|---|
| 1 | p53 | 1. Stabilization; Increase p53 promoter binding activity 2. Pin1 in formation of HMWC and stabilizes p53 | Ser33, Ser315, Thr181; Pro82 | Chk2 | Genotoxic stress, DNA damage Trophoblast invasiveness |
| 2 | Cyclin D1 | Stabilization; localization and transcription | Thr286 | Block Socs-1 ub-mediated proteolysis | Cell proliferation/ cancers |
| 3 | Tau | 1. Dephosphorylated at Thr231 2. Pin1 knockdown or KO increased WT tau protein stability in vitro | Thr231 | | Tauopathy |
| 4 | β-Catenin | Stability; localization and transactivation | Ser246 | Could stabilize β-catenin by inhibiting GSK-3β dependent degradation | Cell proliferation/cancers |
| 5 | c-Jun | Transcriptional activity | Ser63/Ser73 | JNK | Breast cancer; AML |
| 6 | p65/NF-kB | Nuclear translocation; stability | Thr254 | | Cytokines; Hepatocyte NF-kappaB activation |
| 7 | p73 | Stabilizing, transcriptional activity | Ser412, Thr442 and Thr482 | c-Abl and p300 | Genotoxic stress |

TABLE 2A-continued

Pin1 targets where Pin1 prevents protein from degradation

| | PROTEIN NAME | PIN1 FUNCTION | PIN1 BINDING MOTIF | KINASE/ PHOSPHATASE | PATHWAYS/ DISEASES/ MECHANISM |
|---|---|---|---|---|---|
| 8 | Synphilin-1 | Facilitates Lewy Body formation; stabilizes alpha-synuclein | Ser211 and Ser215 | casein kinase II | Parkinson disease |
| 9 | c-Fos | Transcriptional activation | C-terminal | ERK | |
| 10 | Sil | No impact on Sil spindle checkpoint | | | Unknown |
| 11 | p54nrb | | Thr412, Thr430 and Thr452 | Cdk1 | |
| 12 | Bruton tyrosine kinase (Btk) | Mediates Btk degradation | Ser21 an Ser115 | | Tyrosine kinase |
| 13 | AUF1 | Regulates GM-CSF mRNA; AUF1, AU rich element-binding protein | Ser83 | | |
| 14 | $BIM_{EL}$ | Stabilize $BIM_{EL}$ and induce apoptosis | Ser65 | JIP3, MKK7 and JNK | Neuronal apoptosis |
| 15 | Mcl-1 (Myeloid cell leukemia sequence-1) | 1. Pin1 inhibits Mcl-1 ubiquitination 2. Stabilizes Mcl-1 | Thr163; Thr92 | JNK3 induces Mcl-1 degradation by counting the protective binding of Pin1 Erk phosphorylates Thr92 and Thr163 | Oligodendrocyte apoptosis; Mcl-1 mediated chemoresistance; breast cancer |
| 16 | HBx; Hepatitis B virus encoded protein X | Pin1 overexpression increased the protein stability of HBx | Ser41 | Pin1 binds HBx and enhance hepatocarcinogenesis in HBV-infected hepatocytes | Hepatocarcinogenesis |
| 17 | Origin recognition complex, subunit 1 (ORC1) | Prevents degradation of ORC1 by inactivating mitotic APC complex | | APC; Topo II | Mitotisis; chromosome segregation and for reprogramming replicons |
| 18 | Bcl-2 | 1. Induce changes in the bioactivity of Bcl-2; 2. Prevents dephosphorylation of Bcl-2 | | Possibly mediated by cdc2 | |
| 19 | Erb2 | Stabilize ErbB2 | Ubiquitinated erbB2 | ErbB2 pathway; ubiquitin mediated degradation | Her2-positive breast cancer |
| 20 | PPARγ | Prevents the polyubiquitination of PPARγ through ubiquitin-proteosome pathway | Ser84 | Ras mediated kinase | Macrophages mediated atherosclerosis |
| 21 | Cep55 | Increased Cep55 stability | Ser425, Ser428 | Cdk1, Plk1 | Mitosis and cytokinesis |
| 22 | Spt23 | Ess1 stabilizes Spt23 | Ser654 | | Unsaturated fatty-acid synthesis |
| 23 | p27 | Pin1 protects p27 from degradation through polyubiquitination mechanism. | Thr187 | Cdk2 | Cell cycle; Cancer |
| 24 | Akt | Regulates Akt protein stability | Thr92, Thr450 | | Oncogenesis |
| 25 | HTLV Tax protein | Increased Tax protein expression; inhibits Tax protein degradation | Ser160 | | Pathogenesis of Human T-cell leukemia virus type 1 (HTLV-1) related diseases |
| 26 | Nanog | Leads to Nanog stability | Ser52, Ser65 | | Stem cells pluripotency; cell renewal |
| 27 | Viral Integrase | Stabilized phospho-HIV-1 integrase | Ser57 | JNK | HIV-1 cDNA integration and infection |

TABLE 2B

Pin1 targets where Pin1 enhances degradation of phosphorylated proteins

| | PROTEIN NAME | PIN1 FUNCTION | PIN1 BINDING MOTIF | KINASE/ PHOSPHATASE | PATHWAYS/ DISEASES/ MECHANISM |
|---|---|---|---|---|---|
| 1 | c-Myc | Enhances c-Myc degradation | Thr58 | | Tumorgenesis |
| 2 | Cyclin E | Depletion of Pin1 upregulates cellular level of Cyclin E | Ser384 | Cyclin E-Cdk2 complex | Cell cycle, genomic instability and tumorigenesis |
| 3 | SRC-3/AIB1 | Enhances SRC-3 degradation | N/A | Steroid receptor | |
| 4 | RARα | Induces its degradation | Ser77 | | Retinoic acid receptor; |
| 5 | IRF3 | Promote its degradation via the ubiquitin-proteasome pathway. | Ser339 | | Host antiviral responses during virus infection |
| 6 | Che-1 | Conformational changes induced by Pin1 are requested for Che-1/HDM2 interaction | Thr144 | | p53 transcription; DNA damage apoptotic pathway |
| 7 | Pim-1 protein kinase | Binding of Pin1 leads to a decrease in the protein level of Pim-1 | N/A | PP2A | Elevated in lymphomas leukemias and prostate cancer through c-Myc pathway |
| 8 | Promyelocytic leukemia protein (PML) | Binds to phosphorylated C terminus of PML and enhances PML degradation | C-terminal of PML (Ser403, Ser505, Ser518 and Ser527) | | Breast cancer; hydrogen peroxide-induced death; cell proliferation |
| 9 | FOXO | A novel negative FOXO regulator, interconnecting FOXO phosphorylation and monoubiquitination in response to cellular stress to regulate p27 | | | Oxidative stress |
| 10 | Silencing mediator for retinoic acid and thyroid hormone receptor (SMRT) | Pin1 destabilizes SMRT | Ser1241, Thr1445, Ser1469 | Her2/Neu/ErbB2 receptor; Cdk2 | Human cancer |
| 11 | TRF-1 | Pin1 inhibition resulted in decrease TRF1 degradation; | Thr149 | Cdk | Cancer; ageing |
| 12 | G protein-coupled receptor kinase 2 (GRK2) | Promotes GRK2 degradation | Ser670 | CDK2-cyclinA | Cell cycle progression; p53 response and the induction of apoptosis |
| 13 | SF-1 | Pin1 promotes SF-1 ubiquitination and degradation | Ser203 | CDK7 | Gonadotropin beta-subunit gene transcription |
| 14 | Sulfotrans-ferase 4A1 (SULT4A1) | Pin1 destabilizes SULT4A1 | Thr8, Thr11 | ERK1 and PP2A | Metabolism of endogenous and exogenous compounds |
| 15 | Smad2/ Smad3 | Reduced Smad2/3 protein levels | Thr179, Ser204, Ser208, Ser213 (Smad3 linker domain) | Smurf2 with Smads and enhanced Smad ubiquitination | TGF-β signaling |
| 16 | MEF2C | Pin1 decreases MEF2C stability | Ser98/Ser110 | | Muscle terminal differentiation |

TABLE 2C

Pin1 targets where Pin1 regulates target phosphorylation/dephosphorylation/other modifications

| | PROTEIN NAME | PIN1 FUNCTION | PIN1 BINDING MOTIF | KINASE/ PHOSPHATASE | PATHWAYS/ DISEASES/ MECHANISM |
|---|---|---|---|---|---|
| 1 | Tau | Enhance dephosphorylation at Thr231 | Thr231 | | Neuronal differentiation; stress induced; Alzheimer disease |
| 2 | Raf-1 | Dephosphorylation by PP2A | N.A. | Ras/MAP Kinase | |
| 3 | Type-1 protein phosphatase Inhibitor-2 (I-2) | Cycling phosphorylation in mitotic | Thr72 | CDK1-cyclin B | Entry and exit in mitotic |
| 4 | TGF-β1 mRNA | Decay, accumulation and translation of TGF-β1 mRNA in Eosinophils | | | Chronic asthma |
| 5 | K-homology splicing regulator protein (KSRP) | parathyroid hormone (PTH) mRNA stability | Ser181 | | |

TABLE 3

Pin1-targets for promoting tumorigenesis

| Substrates | Function | Binding Sites | Effects | Activation/ Inactivation |
|---|---|---|---|---|
| AIB1/SRC3 | Transactivator | — | Activity | + |
| Akt | Protein kinase | pThr$^{92/450}$-Pro | Stability | + |
| Bax | Apoptosis | pThr$^{167}$-Pro | Activity | − |
| Bcl-2 | Antiapoptic protein | — | Stability | − |
| Btk | Tyrosine kinase | pSer$^{21/115}$-Pro | Stability | − |
| β-catenin | Transcription factor | pSer$^{246}$-Pro | Localization, stability | + |
| C/EBP | Transcription factor | — | Activity | − |
| Cyclin D1 | Transcription factor | pThr$^{286}$-Pro | Localization, stability | + |
| Daxx | Apoptosis | pSer$^{178}$-Pro | Stability | − |
| FAK | Tyrosine kinase | pSer$^{910}$-Pro | Activity | + |
| c-Fos | Transcription factor | — | Activity | + |
| FOXO4 | Transcription factor | — | Localization, activity | − |
| GRK2 | G protein receptor | pSer$^{670}$-Pro | Stability | − |
| Hbx | Transactivator | pSer$^{41}$-Pro | Activity, stability | + |
| c-Jun | Transcription factor | pSer$^{63/73}$-Pro | Activity, stability | + |
| Mcl-1 | Apoptosis | pThr$^{92/163}$-Pro | Stability | + |
| c-Myb | Transactivator | pSer$^{528}$-Pro | Activity | + |
| Neu | Growth factor receptor | — | Stability | + |
| NF-κB | Transcription factor | pThr$^{254}$-Pro | Localization, stability | + |
| Notch1 | Growth factor | — | Activity | + |
| p70S6K | Ribosomal S6 kinases | — | Activity | + |
| p53 | Transcription factor | — | Activity, stability | −* |
| Plk1 | Mitotic kinase | — | Binding activity | + |
| PML | Transcription factor | pSer$^{403/505/518/527}$-Pro | Stability | − |
| Raf-1 | Protein kinase | — | Activity | + |
| RARα | Transcriptional regulator | pSer$^{77}$-Pro | Stability | − |
| V-Rel | Transcription factor | pThr$^{254}$-Pro | Localization, stability | + |
| Smad | Transactivator | — | Stability | − |
| SMRT | Transcriptional co-repressor | pSer$^{1241/1469}$, Thr$^{1445}$-Pro | Stability | − |

TABLE 3-continued

Pin1-targets for promoting tumorigenesis

| Substrates | Function | Binding Sites | Effects | Activation/Inactivation |
|---|---|---|---|---|
| Stat3 | Transcription factor | pSer$^{727}$-Pro | Activity | + |
| Tax | Viral oncoprotein | pSer$^{160}$-Pro | Activity, stability | + |
| Pin2/TRF1 | Telomere regulation | pThr$^{149}$-Pro | Stability | − |

The importance of phosphorylation-independent prolyl isomerization has also been documented. For example, the PPIase CypA catalyzes the cis-trans isomerization of the prolyl bond at position Gly237-Pro238 of the Crk protein. Other PPIase substrates isomerized in a phosphorylation-independent or -dependent manner include, without limitation, steroid receptors, c-Myb, H3P30, H3P38, Itk, 5-hydroxytryptamine type 3 (5-HT3) receptors, the phage tip protein G3P, the Gag polyprotein of the human immunodeficiency virus-1 (HIV-1) virion, intracellular calcium release channel, CrkII/CrkL proteins, centrosome protein 55 kDa (Cep55), the retroviral Rd proteins, PKB/Akt, human T-cell leukemia virus type 1 (HTLV-1) Tax oncoprotein, Stat3, HER2/Neu, Notch, FAK, FOXO, PML, C/EBP, and SMRT. Deregulation of PPIase activity (e.g., the upregulation or downregulation of PPIase activity (e.g., an increase or decrease in PPIase activity)) may, for example, result in a greater cis or trans content of Ser/Thr-Pro motifs present in PPIase substrates, which may affect the function of the PPIase substrate and result in the development of, e.g., cellular proliferation disorders, neurological disorders, asthma, or aging-associated disorders.

Conformation-Specific Antibodies

The present invention describes methods and compositions for the generation of conformation-specific antibodies. Conformation-specific antibodies may, for example, specifically bind to the cis or trans conformation of a polypeptide. In a specific embodiment, the conformation-specific antibody of the invention may bind to the cis conformation of a phosphorylated or nonphosphorylated Xaa-Pro motif of a polypeptide. The conformation-specific antibody may, alternatively, bind to the trans conformation of a phosphorylated or nonphosphorylated Xaa-Pro motif of a polypeptide. The Xaa-Pro motif may be a phosphorylated Ser/Thr-Pro motif of a polypeptide (e.g., a Pin1 substrate). The binding of a conformation-specific antibody to its antigen (e.g., a Pin1 substrate) may be useful in the treatment, diagnosis, or monitoring of a disorder or the progression of a disorder.

Antigens

Conformation-specific antibodies of the present invention may be generated using immunogenic antigens (e.g., antigenic peptides) containing, for example, a phosphorylated or nonphosphorylated Xaa-Pro motif, where Xaa is any amino acid residue (e.g., serine or threonine) fixed in a particular conformation (e.g., the cis or trans conformation) or in mixed cis and trans conformations or any other motif or amino acid sequence that is capable of cis/trans isomerization. For example, the cis or trans content of phosphorylated or nonphosphorylated Ser/Thr-Pro-containing antigenic peptides of the invention may be fixed by stereoselective synthesis of (Z)- and (E)-alkene mimics by Still-Wittig and Ireland-Claisen rearrangements (J. Org. Chem., 68: 2343-2349, 2003; hereby incorporated by reference). Alternatively, the cis or trans content of phosphorylated or nonphosphorylated Ser/Thr-Pro-containing antigenic peptides of the invention may be increased or fixed by substituting a proline amino acid residue with a proline analog. Proline analogs include, without limitation, homoproline, pipecolic acid (Pip), 5,5-dimethyl proline (DMP), azetidine-2-carboxylic acid (Aze), tert-butyl-L-proline (TBP), trans-4-fluoro-L-proline (t-4F-Pro), 2,2-dimethyl-thiazolidine (Thz), and cis-4-fluoro-L-proline (c-4F-Pro). The cis or trans content of a given antigen may be analyzed by, for example, nuclear magnetic resonance (NMR) analysis.

Antigenic peptides of the invention may contain a phosphorylated or nonphosphorylated Xaa-Pro motif, wherein Xaa is any amino acid residue (e.g., serine or threonine), which is capable of cis/trans isomerization. The antigenic peptide may contain the amino acid residues of the Xaa-Pro motif of a Pin1 substrate (examples of which are provided in Table 1), with the proline residue substituted for a proline analog. The antigenic peptide may also contain the amino acid residues of the Xaa-Pro motif of a full-length polypeptide, wherein the full-length polypeptide is any of the peptides in tables 1, 2A-2C, and 3, including the following polypeptides or any isoform thereof: steroid receptors, c-Myb (GenBank Accession No. AAA52032), Itk (GenBank Accession No. BAA02873), 5-hydroxytryptamine type 3 (5-HT3) receptors (Gen Bank Accession Nos. NP_001157118, NP_570126, and NP_872395), the phage tip protein G3P, the Gag polyprotein of the human immunodeficiency virus-1 (HIV-1) virion (GenBank Accession No. AAD39400), intracellular calcium release channel, CrkII/CrkL proteins (GenBank Accession Nos. NP_058431, NP_005197, CAG30309, and CAA42199), centrosome protein 55 kDa (Cep55) (GenBank Accession Nos. NP_001120654 and NP_060601), the retroviral Rel proteins (GenBank Accession No. NP_002899 and ABC40747), PKB/Akt (GenBank Accession No. NP_001014432 and NP_005154), human T-cell leukemia virus type 1 (HTLV-1) Tax oncoprotein (GenBank Accession No. P03409), Stat3 (GenBank Accession No. AAK17196), HER2/Neu (GenBank Accession No. AAD14920), Notch (GenBank Accession Nos. NP_476859), FAK (GenBank Accession Nos. AAA58469, NP_005598, and NP_722560), FOXO (GenBank Accession No. 016850), PML (GenBank Accession No. AAB19601), C/EBP (GenBank Accession Nos. AAA28415 and AAB33475), and SMRT (GenBank Accession Nos. Q9WU42 and AAC50236). The antigenic peptide may further include additional residues surrounding the Xaa-Pro motif of the full-length polypeptide. For example, the antigenic peptide may include the 3-10 amino acid residues N-terminal to the Xaa residue of a full-length polypeptide and the 3-10 amino acid residues C-terminal to the proline of a full-length polypeptide.

The antigenic peptide of the invention may be, for example, at least 4, 5, 6, 7, or 8 amino acid residues in length. The antigenic peptide may be between 8 and 20 amino acid residues in length (e.g., 8, 9, 10, 11, 12, 13, 14, 15, 16, 17, 18, 19, or 20 amino acids residues in length) or may be over 20 amino acid residues in length.

Such antigens may be produced and purified by any of a variety of methods known to one of skill in the art. Antigenic peptides may be produced and purified by, e.g., solid-phase chemical synthesis, in vitro transcription/translation, or by recombinant technology. The antigenic peptides may optionally be chemically coupled to a carrier protein or the peptides may be generated as fusion proteins to increase antigenicity. Antigenic peptides may be screened based upon their ability to induce the production of conformation-specific antibodies. In this respect, such screening techniques may include, but are not limited to, enzyme-linked immunosorbant assays (ELISA), immunoprecipitation, or other immunoassays.

Exemplary antigens useful in the production of conformation-specific antibodies include antigens containing a phosphorylated or nonphosphorylated Ser/Thr-homoproline, Ser/Thr-Pip, Ser/Thr-DMP, Ser/Thr-Aze, Ser/Thr-TBP, Ser/Thr-t-4F-Pro, Ser/Thr-c-4F-Pro motif, Ser/Thr-THZ. Specific examples of such antigens include, e.g., pThr668-Pip and pThr668-DMP APP peptide (VDAAV-pThr668-Pro-EE-RHLSK; SEQ ID NO: 3),pThr231-Pip tau peptide, pThr231-THZ tau peptide (KKVAVVR-(pT231)-(Thz)-PKSPS; SEQ ID NO: 2) and pThr231-DMP tau peptide (KVAVVR-pThr231-Pro-PKSPS; SEQ ID NO: 4). Other exemplary antigens are also describedin U.S. Patent Application Publication No. 2008/0058276, hereby incorporated by reference. Such peptides may be used as antigens for generating an antibody in a human and consequently, e.g., inducing an immune response in the human against the antigenic peptide resulting in, optionally, long lasting vaccination.

Therapeutic Formulations

The invention includes proline-analog-containing antigenic peptides including a Xaa-Pro motif, pharmaceutical, and methods of their use and preparation. Such pharmaceutical compositions resulting in a lasting immune response against the antigenic peptides are vaccine compositions. Prophylactic vaccines can be used to reduce the likelihood of a subject acquiring a disorder associated with a deregulation of PPIase activity (e.g., Alzheimer's disease); therapeutic vaccines may be used to treat subjects diagnosed with such disorders.

The antigenic peptides of the invention can be used, for example, in vaccination methods to induce an immune response against a particular conformation of a PPIase target protein. Such an immune response is useful, e.g., to treat or decrease the risk of developing a disorder associated with a deregulation of PPIase activity (such disorders include, for example, cellular proliferation disorders (e.g., cancer), neurological disorders (e.g., Alzheimer's disease), aging-related disorders, asthma, microbial infections (e.g., viral infections (e.g., HIV infections)), and aging or other aging-related disorders). These methods can be prophylactic, in which case they are carried out on humans not having, and/or not exhibiting symptoms of a disorder associated with a deregulation of PPIase activity, but at risk of developing such a disease. The methods can also be therapeutic, in which they are carried out on subjects already exhibiting symptoms of a disorder associated with a deregulation of PPIase activity. Further, antigenic peptides of the invention can be used in combination with each other, other vaccines, passive vaccination, and other therapeutic agents. The subjects treated according to the methods of the invention include humans.

Numerous pharmaceutically acceptable solutions for use in vaccine preparation are well known and can readily be adapted for use in the present invention by those of skill in this art (see, e.g., *Remington's Pharmaceutical Sciences* (18$^{th}$ edition), ed. A. Gennaro, 1990, Mack Publishing Co., Easton, Pa.).

The antigenic peptides of the invention can be administered using methods that are well known in the art, and appropriate amounts of the antigenic peptides to be administered can readily be determined by those of skill in the art. What is determined to be an appropriate amount of antigenic peptide to administer can be determined by consideration of factors such as, e.g., the size and general health of the subject to whom the virus is to be administered.

All antigenic peptides of the invention can be administered by, for example, intradermal, subcutaneous, intramuscular, intraperitoneal, or oral routes. In specific examples, dendritic cells are targeted by intradermal or transcutaneous administration, by use of, for example, microneedles or microabrasion devices. Further, the vaccines of the invention can be administered in a single dose or, optionally, administration can involve the use of a priming dose followed by a booster dose that is administered, e.g., 2-6 months later, as determined to be appropriate by those of skill in the art.

Optionally, adjuvants that are known to those skilled in the art can be used in the administration of the viruses and vectors of the invention. Adjuvants that can be used to enhance the immunogenicity of the antigenic peptides include, for example, liposomal formulations, synthetic adjuvants, such as (e.g., QS21), muramyl dipeptide, monophosphoryl lipid A, polyphosphazine, CpG oligonucleotides, or other molecules. Optionally, a patch containing a layer of an appropriate toxin-derived adjuvant, can be applied over the injection site. Toxin promotes local inflammation attracting lymphocytes, which leads to a more robust immune response.

Conformation-specific antibodies can be used in combination with the antigenic peptides of the invention in the treatment, inhibition, or prevention of disorders associated with the deregulation of PPIase (e.g., Pin1) activity (see e.g., the antibodies described in PCT/US10/54077, herein incorporated by reference in its entirety). The conformation-specific antibodies may also be used to ameliorate symptoms of these disorders.

The conformation-specific antibodies can be formulated and administered in a variety of ways (e.g., routes known for specific indications, including, but not limited to, topically, orally, subcutaneously, bronchial injection, intravenously, intracerebrally, intranasally, transdermally, intraperitoneally, intramuscularly, intrapulmonary, vaginally, rectally, intraarterially, intralesionally, parenterally, intraventricularly in the brain, or intraocularly). For example, the pharmaceutical composition containing the conformation-specific antibody may be in the form of a pill, tablet, capsule, liquid, or sustained-release tablet for oral administration; a liquid for intravenous or subcutaneous administration; a polymer or other sustained-release vehicle for local administration; or an ointment, cream, gel, liquid, or patch for topical administration.

The conformation-specific antibodies can be administered in conjunction with an adjuvant, for example, cytokines, lymphokines, and chemokines (e.g., IL-2, GM-CSF, IL-12, γ-interferon, IP-10, MIP1β, and RANTES). When the conformation-specific antibodies are used as therapeutic vaccines, the compositions can be administered in conjunction with known therapeutics.

The preparation of compositions containing one or more antibodies, antibody fragments, sFv molecules, Fab, scFv, dAb, VHH therapeutic antibody fragments, or other molecules described, e.g., in Enever et al. (Current Opinion in Biotechnologh 2009, 20:405-411), which is herein incorporated by reference in its entirety, or combinations thereof, as the active ingredient is generally known to those of skill in the art. Typically, such compositions are prepared as injectables (e.g., either as liquid solutions or suspensions or as solid forms suitable for solution or suspension in liquids prior to injection). The compositions will generally also include one or more pharmaceutically acceptable carriers. The compositions may be emulsified or the active ingredient (e.g., the conformation-specific antibody) may be encapsulated in a liposome. In addition, the vaccine compositions can be given as a single dose or as multiple dosages. The dosage regimen may be determined based on the particular needs of the subject to be treated.

Methods for preparing compositions for conferring passive immunity to a subject are described, for example, in WO 83/00229 and also reviewed in, e.g., Casadevall et al., *Nat. Rev. Microbiol.* 2:695-703 (2004); Bayry et al., *Trends Pharmacol. Sci.* 25:306-10 (2004); and Dunman et al., *Curr. Opin. Pharmacol.* 3:486-96 (2003), hereby incorporated by reference in their entirety.

Combination Therapies

The antigenic peptides of the invention may be provided in conjunction (e.g., before, during, or after) with additional therapies to treat a disorder (e.g., a cellular proliferation disorder, a neurological disorder, asthma, or a microbial infection). Treatment therapies that can be used in combination with the methods of the invention include, but are not limited to, chemotherapeutic agents, anti-inflammatory agents, antimicrobial agents, analgesics and anesthetics, bronchodilators, agents for the treatment of neurological disorders, and PPIase inhibitors.

Chemotherapeutic Agents

Any suitable chemotherapeutic agent may be administered in combination with the antigenic peptides of the invention. Chemotherapeutic agents suitable for the composition described herein include, e.g., asparaginase, bleomycin, busulfan carmustine (BCNU), chlorambucil, cladribine (2-CdA), CPT11, cyclophosphamide, cytarabine (Ara-C), dacarbazine, daunorubicin, dexamethasone, doxorubicin (adriamycin), etoposide, fludarabine, 5-fluorouracil (5FU), hydroxyurea, idarubicin, ifosfamide, interferon-α (native or recombinant), levamisole, lomustine (CCNU), mechlorethamine (nitrogen mustard), melphalan, mercaptopurine, methotrexate, mitomycin, mitoxantrone, paclitaxel, pentostatin, prednisone, procarbazine, tamoxifen, taxol-related compounds, 6-thioguanine, topotecan, vinblastine, and vincristine. Exemplary chemotherapeutic agents are listed in, e.g., U.S. Pat. Nos. 6,864,275 and 6,984,654, hereby incorporated by reference.

Anti-Inflammatory Agents

Any suitable anti-inflammatory agent may be administered. Suitable anti-inflammatory agents include, e.g., nonsteroidal anti-inflammatory drugs (e.g., ibuprofen or tacrolimus), cyclooxygenase-2-specific inhibitors such as rofecoxib (Vioxx®) and celecoxib (Celebrex®), topical glucocorticoid agents, and specific cytokines directed at T lymphocyte function. Additional suitable anti-inflammatory agents include flubiprofen, diclofenac, and ketarolac. Anti-inflammatory concentrations known to be effective may be used. For example, ibuprofen may be present in the composition at concentrations sufficient to deliver between 25-800 mg per day to the subject. Exemplary anti-inflammatory agents are listed in, e.g., U.S. Pat. Nos. 7,112,578 and 7,199,119, hereby incorporated by reference.

Antimicrobial Agents

Any of the many known antimicrobial agents can be used in the compositions described herein at concentrations generally used for these agents. Antimicrobial agents include, e.g., antibacterials, antifungals, and antivirals.

Examples of antibacterial agents (e.g., antibiotics) include penicillins (e.g., penicillin G, ampicillin, methicillin, oxacillin, and amoxicillin), cephalosporins (e.g., cefadroxil, ceforanid, cefotaxime, and ceftriaxone), tetracyclines (e.g., doxycycline, minocycline, and tetracycline), aminoglycosides (e.g., amikacin, gentamycin, kanamycin, neomycin, streptomycin, and tobramycin), macrolides (e.g., azithromycin, clarithromycin, and erythromycin), fluoroquinolones (e.g., ciprofloxacin, lomefloxacin, moxifloxacin, and norfloxacin), and other antibiotics including chloramphenicol, clindamycin, cycloserine, isoniazid, rifampin, and vancomycin. Exemplary antimicrobial agents are listed in, e.g., U.S. Pat. Nos. 6,830,745 and 7,056,917, hereby incorporated by reference.

Antiviral agents are substances capable of destroying or suppressing the replication of viruses. Examples of antiviral agents include 1-β-D-ribofuranosyl-1,2,4-triazole-3 carboxamide (ribavirin), 9-2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir. Exemplary antiviral agents are listed in, e.g., U.S. Pat. Nos. 6,093,550 and 6,894,033.

Antifungal agents include both fungicidal and fungistatic agents, e.g., amphotericin B, butylparaben, clindamycin, econaxole, fluconazole, flucytosine, griseofulvin, nystatin, and ketoconazole. Exemplary antifungal agents are listed in, e.g., U.S. Pat. Nos. 5,627,153 and 7,125,842, hereby incorporated by reference.

Analgesics and Anesthetics

Any of the commonly used topical analgesics and anesthetics can be used as therapeutic agents in the invention. Examples of useful anesthetics include procaine, lidocaine, tetracaine, dibucaine, benzocaine, p-buthylaminobenzoic acid 2-(diethylamino) ethyl ester HCl, mepivacaine, piperocaine, and dyclonine. Exemplary anesthetics are listed in, e.g., U.S. Pat. Nos. 6,562,363 and 6,569,839, hereby incorporated by reference.

Analgesics include opioids such as, e.g., morphine, codeine, hydrocodone, and oxycodone. Any of these analgesics may also be co-formulated with other compounds having analgesic or anti-inflammatory properties, such as acetaminophen, aspirin, codeine, naproxen, and ibuprofen. Exemplary analgesics are listed in, e.g., U.S. Pat. Nos. 6,869,974 and 7,202,259, hereby incorporated by reference.

Bronchodilators

Any commonly used bronchodilator can be used as a therapeutic agent in the invention described herein. Examples of useful bronchodilators include, e.g., pirbuterol, epinephrine, albuterol, salbutamol, salmeterol, or levalbuterol. Exemplary bronchodilators are listed in, e.g., U.S. Pat. Nos. 4,489,078, 4,591,588, 4,734,413, 6,299,863, and 6,555,583, hereby incorporated by reference.

Agents for the Treatment of Neurological Disorders

Agents for the treatment of neurological disorders may be used in combination with the therapeutic compositions described herein. Exemplary agents used for the treatment of such disorders include haloperidol, carbamazepine, valproate, donepezil, galanthamine, NMDA antagonists (e.g., memantine), PDE4 inhibitors (e.g., Ariflo), γ-secretase inhibitors, β-secretase inhibitors, GSK-3-α inhibitors, compounds which inhibit the aggregation of Aβ, carbidopa/levodopa, entacapone, tolcapone, pramipexole, ropinerole, pergolide, bromocriptine, selegeline, amantadine, vitamin E, amantadine, coenzyme Q, and anticholingergic agents.

PPIase Inhibitors

PPIase inhibitors include, for example, PiA (2,7-dimethylbenzophenanthroline-1,3,6,8(2H,7H)-tetrone), PiB (diethyl-1,3,6,8-tetrahydro-1,3,6,8-tetraoxobenzo-phenanthroline-2,7-diacetate), PiJ (diethyl-1,3,8,10-tetrahydro-1,3,8,10-tetraoxo-anthra[2,1,9-def:6,5,10-d'e'f']diisoquinoline-2,9-diacetate), cyclosporin A, FK506, ascomycin, and rapamycin. Additional PPIase inhibitors are described in U.S. Pat. No. 6,462,173 and U.S. Patent Application Publication No. 2004/0171019, hereby incorporated by reference.

Diagnostics

The present invention features methods and compositions to treat, diagnose, and monitor the progression of a disorder described herein (e.g., a cellular proliferation disorder, a neurological disorder, an aging-related disorder, asthma, or a microbial infection). The methods and compositions can include the detection and measurement of, for example, Pin1 substrates (or any fragments or derivatives thereof) containing a phosphorylated Ser/Thr-Pro motif in a cis or trans conformation. The methods can include measurement of absolute levels of the Pin1 substrate in a cis or trans conformation as compared to a normal reference. For example, a serum level of a Pin1 substrate in the cis or trans conformation that is less than 5 ng/ml, 4 ng/ml, 3 ng/ml, 2 ng/ml, or less than 1 ng/ml serum is considered to be predictive of a good outcome in a patient diagnosed with a disorder (e.g., a disorder associated with a deregulation of Pin1 activity). A serum level of the substrate in the cis or trans conformation that is greater than 5 ng/ml, 10 ng/ml, 20 ng/ml, 30 ng/ml, 40 ng/ml, or 50 ng/ml is considered diagnostic of a poor outcome in a subject already diagnosed with a disorder, e.g., associated with a deregulation of Pin1 activity.

For diagnoses based on relative levels of substrate in a particular conformation (e.g., a Pin1 substrate in the cis or trans conformation), a subject with a disorder (e.g., a disorder associated with a deregulation of PPIase activity) will show an alteration (e.g., an increase of 10%, 20%, 30%, 40%, 50%, 60%, 70%, 80%, 90%, or more) in the amount of the substrate in, for example, the cis conformation. A normal reference sample can be, for example, a prior sample taken from the same subject prior to the development of the disorder or of symptoms suggestive of the disorder, a sample from a subject not having the disorder, a sample from a subject not having symptoms of the disorder, or a sample of a purified reference polypeptide in a given conformation at a known normal concentration (i.e., not indicative of the disorder).

Standard methods may be used to measure levels of the substrate in any bodily fluid, including, but not limited to, urine, blood, serum, plasma, saliva, amniotic fluid, or cerebrospinal fluid or diseased tissues such as cancer tissue biopsy. Such methods include immunoassay, ELISA, Western blotting, and quantitative enzyme immunoassay techniques.

For diagnostic purposes, conformation-specific antibodies may be labeled. Labeling of the antibody is intended to encompass direct labeling of the antibody by coupling (e.g., physically linking) a detectable substance to the antibody, as well as indirect labeling the antibody by reacting the antibody with another reagent that is directly labeled. For example, the antibody can be labeled with a radioactive or fluorescent marker whose presence and location in a subject can be detected by standard imaging techniques.

The diagnostic methods described herein can be used individually or in combination with any other diagnostic method described herein for a more accurate diagnosis of the presence or severity of a disorder (e.g., a cellular proliferation disorder or a neurological disorder). Examples of additional methods for diagnosing such disorders include, e.g., examining a subject's health history, immunohistochemical staining of tissues, computed tomography (CT) scans, or culture growths.

Subject Stratification and Monitoring

The diagnostic methods described herein can also be used to identify or stratify patients for conformation-specific therapies using vaccine or antibodies, to monitor the progression of a disorder (e.g., a cellular proliferation disorder or a neurological disorder) during therapy or to determine the dosages of therapeutic compounds. In one embodiment, the levels of, for example, polypeptides (e.g., Pin1 substrates) with pSer/Thr-Pro motifs in the cis or trans conformation are measured repeatedly as a method of diagnosing the disorder and monitoring the treatment or management of the disorder. In order to monitor the progression of the disorder in a subject, subject samples can be obtained at several time points and may then be compared. For example, the diagnostic methods can be used to monitor subjects during chemotherapy. In this example, serum samples from a subject can be obtained before treatment with a chemotherapeutic agent, again during treatment with a chemotherapeutic agent, and again after treatment with a chemotherapeutic agent. In this example, the level of Pin1 substrate with a pSer/Thr-Pro motif in the cis conformation in a subject is closely monitored using conformation-specific antibodies of the invention and, if the level of Pin1 substrate with a pSer/Thr-Pro motif in the cis conformation begins to increase during therapy, the therapeutic regimen for treatment of the disorder can be modified as determined by the clinician (e.g., the dosage of the therapy may be changed or a different therapeutic may be administered). The monitoring methods of the invention may also be used, for example, in assessing the efficacy of a particular drug or therapy in a subject, determining dosages, or in assessing progression, status, or stage of the infection.

EXAMPLES

Example 1

Synthesis of Conformation-specific Antibodies

We describe the synthesis and purification of conformation-specific antibodies recognizing cis- or trans-pT231-P tau.

Since about 90% of pSer/Thr-Pro motifs in a synthetic peptide are in trans, a major challenge is to increase the cis content in the antigen. We have identified a non-natural amino acid that has a similar structure to proline, homoproline (PIP). PIP dramatically increases the cis content of the synthetic peptide to about 74%. Peptides containing PIP or similar proline analogs (e.g., dmP) are synthesized according to standard techniques. These peptides are fragments of full-length phosphorylated proteins (e.g., Pin1 substrates) containing Xaa-Pro motifs (e.g., tau protein or APP) with the proline of the Xaa-Pro motif of the full-length polypeptide replaced by a proline analog in the synthetic peptide. These peptides are used to immunize host animals (e.g., rabbits).

Figure 3:
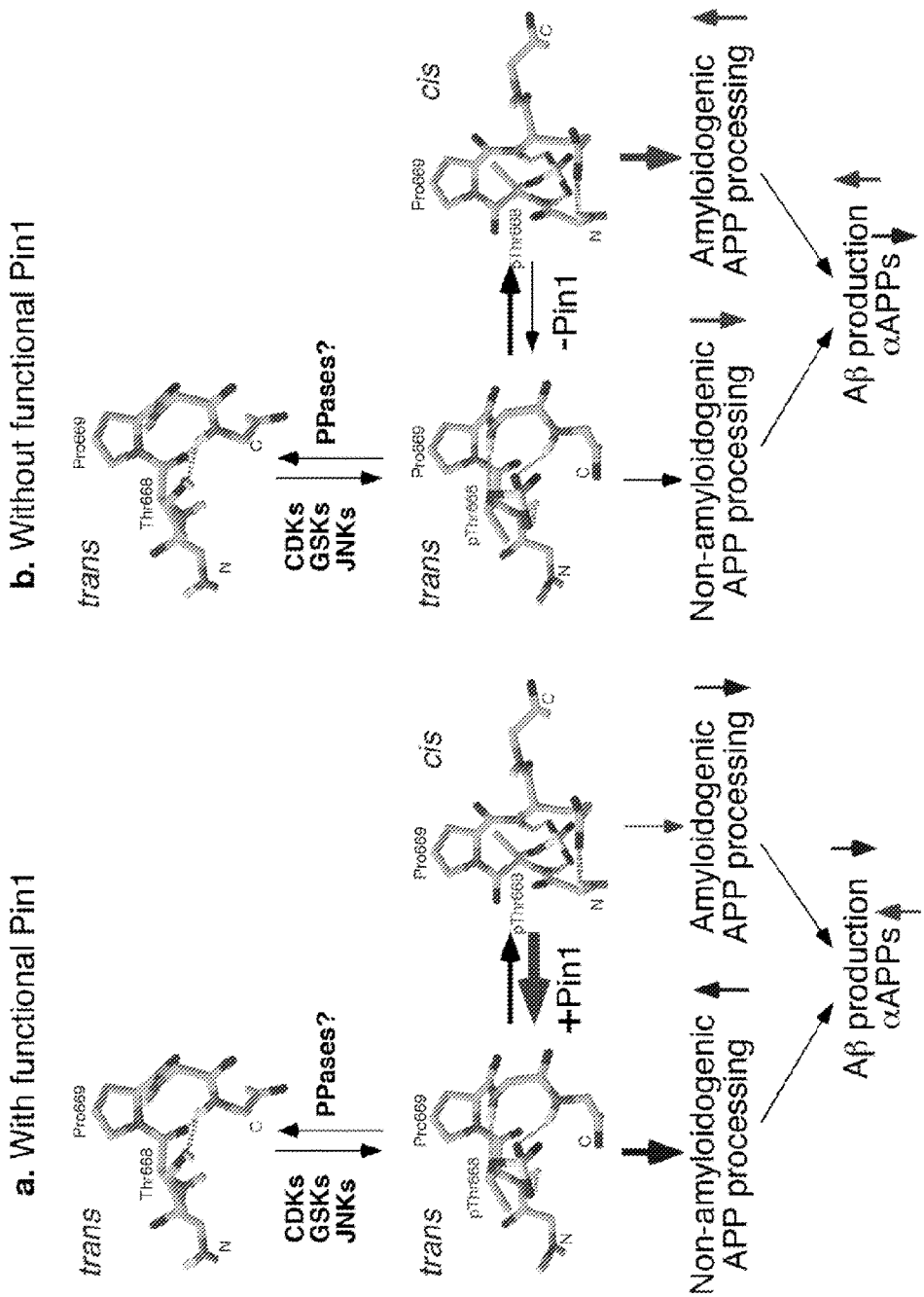
FIG. 3 is a schematic diagram showing that phosphorylation-dependent prolyl cis-trans isomerization acts as a molecular timer in amyloid precursor protein (APP) processing and Aβ production in Alzheimer's disease (AD). Phosphorylation of APP on the Thr668-Pro motif occurs during mitosis in the cell cycle and is also increased in AD brains. Before phosphorylation, the Thr668-Pro motif in APP is in a trans conformation in a helix cap structure. Although the pThr668-Pro motif of APP is likely phosphorylated in trans by upstream kinases, it has a tendency to be in cis, with the overall content being ~10% due to both destabilization of the trans isomer by loss of hydrogen bonds resulting from a local unfolding of a helix cap and to stabilization of the cis isomer by hydrogen bonds involving the phosphate. Pin1 accelerates both $k_{cis\ to\ trans}^{cat}$ and $k_{trans\ to\ cis}^{cat}$ by several orders of magnitude over the typical uncatalyzed isomerization rates for pThr-Pro peptides, resulting in a dramatic reduction in the average lifetime of both the cis (~0.05 s) and trans (~0.5 s) isomeric states to fractions of a second, with the catalyzed cis to trans rate being 10-fold faster than the catalyzed trans to cis rate. This favors more non-amyloidogenic APP processing, reducing Aβ production (FIG. 3A). In contrast, without proper Pin1 function, the cis pThr668-Pro motif may not be isomerized to trans, which might favor more amyloidogenic APP processing and Aβ production (FIG. 3B). Therefore, in collaboration with other AD factors, Pin1 deregulation can promote non-amyloidogenic APP processing and Aβ production.
Figure 4:
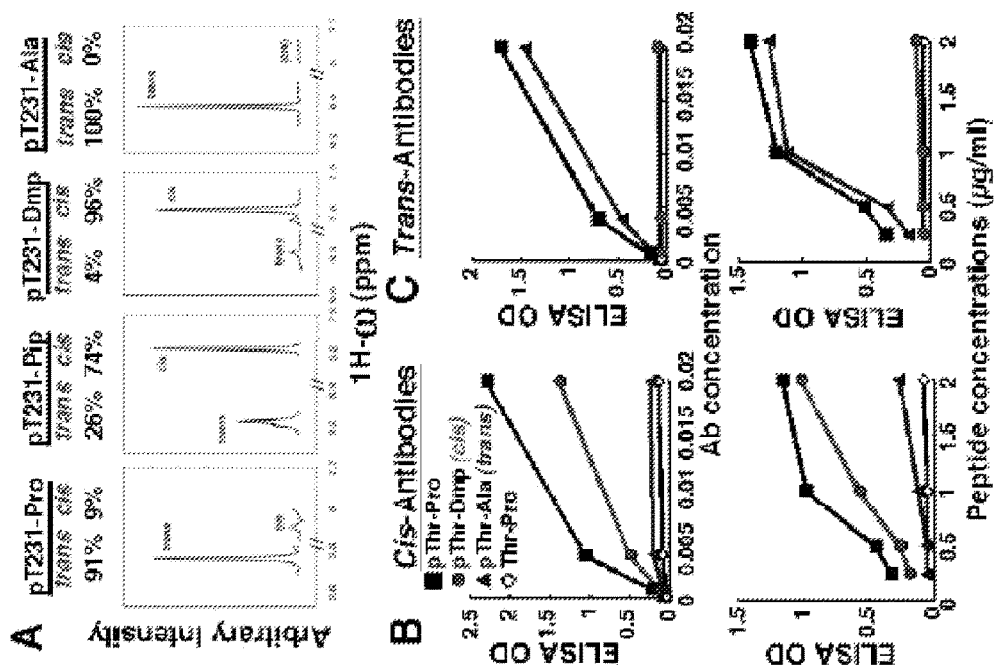
FIG. 4A is a series of graphs showing the prevalence of the cis conformation in the indicated peptides.
FIGS. 4B and 4C are a series of graphs showing results from ELISA showing cis-Abs (4B) or trans-Abs (4C) recognition of the indicated tau peptide.

Since Dmp or Thz can knock Xaa-Dmp or Thz bond in cis, whereas Xaa-Ala is in trans, we synthesized a biotinated pT231-Dmp or -Thz or pT231-Ala tau peptide and confirmed them to be cis or trans by NMR (FIG. 3A), respectively. These peptides were used as affinity columns to separate cis- from trans-specific antibodies, followed by counter-purification with cis or trans pT231-P tau peptide beads to remove any possible contamination. We first used ELISA assay to show that cis-specific antibodies recognized regular pT231-P tau and cis pT231-Dmp tau peptides (FIG. 3), whereas trans specific antibodies recognized regular pT231-P and trans pT231-Ala tau peptides (FIG. 3C) with little cross-reactivity (FIGS. 3B and 3C). Neither antibodies recognized non-phosphorylated tau peptide (FIGS. 3B and 3C). Thus, cis and trans pT231-tau antibodies are conformation-specific.

To separate cis- and trans-specific antibodies generated by the immunized animals, we synthesized a biotinated pT231-(L-5,5-dimethylproline) (dmP) tau peptide and conjugated it to an affinity column and purify the cis- and trans-specific antibodies. Importantly, the cis-specific antibodies, but not trans-specific antibodies, recognize the pT231-dMP tau peptide. Thus, the pT231-dmP column bound cis-specific antibodies, while trans-specific antibodies were found in the unbound fraction. The cis-specific antibody was eluted from the column using a Thr-Pro peptide. To obtain purified trans-specific antibody, the unbound fraction containing the trans-specific antibody was repurified with a pThr-Pro peptide, as trans-specific antibody binds pThr-Pro.

We found that both cis- and trans-specific tau antibodies recognized pT231-Pro tau peptide with similar intensity. Neither cis- nor trans-specific antibodies recognized the nonphosphorylated T231-Pro tau peptide or pT231-Ala tau peptide. Moreover, both cis- and trans-specific antibodies specifically recognized phosphorylated T231-containing tau protein, but not its Thr231Ala point mutant. Thus, cis- and trans-specific pT231 tau antibodies have the expected properties and specificity with little cross-reactivity.

Example 2

Cis pT231-P Tau Lost Function to Promote Microtubule Assembly and was More Resistant to Dephosphorylation and Degradation than the Trans We used the above-generated antibodies to test the hypothesis that cis pT231-tau might not promote MT function and might be more resistant to dephosphorylation and degradation. To examine the effects on the ability of p-tau to promote MT assembly, an MT assembly assay was performed using FITC-labeled tubulins. As expected, MT assembly was minimal without tau, but dramatically increased if tau was added. However, this increase was mostly abolished if tau was first phosphorylated on T231 by Cdc2, but was restored if p-tau was dephosphorylated by PP2A. Furthermore, Pin1 restored the ability of p-tau to promote MT assembly. More importantly, the ability of Pin1 to restore p-tau MT function was fully blocked by incubation of Pin1-treated p-tau with the trans antibodies, but not cis antibodies, indicating that blockade of the trans, but not cis conformation prevents p-tau from promoting MT assembly. Thus, cis, but not trans, p-tau loses the function to promote MT assembly and Pin1 catalyzes cis to trans isomerization to restore p-tau MT function. Given that the tau phosphatase PP2A is conformation-specific, preferentially dephosphorylating pS/T-P motifs in trans, we then assayed the sensitivity of cis and trans pT231-tau to PP2A using the conformation-specific antibodies. Trans, but not cis, pT231-tau peptide was readily dephosphorylated by PP2A in a time-dependent manner.

Finally, to examine whether these two p-tau conformations have any differences in protein degradation, we compared degradation of cis- and trans-pT231-P tau proteins in vitro. SY5Y cells overexpressing human tau were subjected to cycloheximide (CHX) chase to stop new protein synthesis and were analyzed by western blot using the cis and trans antibodies. The cis conformation was much more stable than the trans. The CHX chase experiments were also performed using cultured brain slice from Tau-Tg mice, a model that maintains the three dimensional architecture and synaptic connections of the brain closely resembling the in vivo situation. Again, the cis was much more stable than the trans. These results supported our hypothesis that cis pT231-P tau loses function to promote microtubule assembly and is more resistant to dephosphorylation and degradation than the trans.

Example 3

Pin1 Overexpression Decreased Cis-pT231-tau, but Increased Trans-pT231-tau in Tau-Tg Mice We found that the cis/trans ratio of pT231-tau increases during tauopathy development, but that overexpression of Pin1 can reduce the amount of tau peptide that is in the cis conformation. An AD mouse model overexpressing human wild-type tau under the Thy1 promoter (Tau-Tg) develops an age-dependent tauopathy phenotype. We found that only the cis, but not trans, pT231-Tau were dramatically accumulated in aged brains. However, when Tau-Tg mice were crossed with Thy1-Pin1 transgenic mice, endogenous tau levels were reduced. Pin1 overexpression not only effectively prevented accumulation of cis pT231-Tau, but also increased trans, pT231-Tau, as documented both by immunostaining and immunoblotting analyses. These conformation-specific results provide the first in vivo evidence that Pin1 promotes cis-to-trans isomerization of pTau to protect against tangle formation. These results also suggest that it is not general pT231-Tau, but rather its cis/trans ratio, that is pathologically significant in the tauopathy development in mouse models.

Example 4

Elevation of Cis-, but not Trans-, pT231-tau in Degenerated Human Brains

We found that cis-, but not trans-, pT231-tau is elevated in subjects with mild cognitive impairment (MCI) and AD. To examine changes in pT231-tau conformation at different AD stages in humans, we immunostained normal and AD brain tissue with cis- or trans-specific tau antibodies. There was little cis- or trans-pT231-tau present in normal human brains. In AD, trans-pT231-tau was barely detectable. Even at Braak VI, very few neurons displayed a strong trans-pT23'-tau signal. In contrast, cis-pT23'-tau was detected and found to accumulate in somatodendritic regions of neurons at Braak III or IV (MCI) brain tissue. Furthermore, cis-pT23'-tau continued to accumulate as Braak stage increased. These results showed that cis-pT231-tau is accumulated at an early stage of degeneration before AD pathologies develop.

To confirm these results, we compared brain tissue immunostained with either cis-pT231-tau antibodies or mAb TG3.

Brain tissue immunostained with TG3 showed strong signals only in Braak stage V AD brain tissue, but not in Braak III or IV MCI brain tissue, confirming that TG3 recognizes tau phosphorylated on T231 only in the AD-specific conformation. However, cis-pT231-tau was readily detected in Braak III or IV MCI brain tissue. These results show that cis-, but not trans-, pT231-tau is elevated at very early stages of AD and further accumulates as the disease progresses in human brains.

Example 5

The Cis/Trans Ratio of pT231-tau in the Cerebrospinal Fluid (CSF) of AD Patients We found that the cis/trans ratio of pT231-tau in the cerebrospinal fluid (CSF) was elevated in late AD patients with small individual variations. To examine whether it is possible to assay cis- and/or trans-pT231-tau in CSF, we obtained postmortem CSF from five late AD patients and two control subjects and performed an assay using the INNOTEST hTau ELISA kit (Innogenetics) to detect the presence of cis- and trans-pT231-tau. The detection antibodies in the kit were replaced with cis- or trans-pT231-tau polyclonal antibodies. Although neither cis- nor trans-pT231-tau was detectable in control CSF, cis- and trans-pT231-tau were detected in the CSF of AD patients (p<0.0001) and showed large individual variations. However, variations in the cis/trans ratio values of pT231-tau were smaller (from >10-fold to <0.5-fold). These results show that, unlike the pT231-tau peptide, the cis- and trans-pT231-tau present in CSF do not have the same immunoreactivity to the cis and trans antibodies, indicating the feasibility of quantifying cis- and trans-pT231-tau proteins in CSF. These results show that both cis- and trans-pT231-tau proteins are elevated in the CSF of AD patients and suggest that cis/trans ratio of pT231-tau can serve as a biomarker for AD.

Example 6

Monoclonal Antibodies Recognizing Cis- and Trans-pT231-tau

To establish cis- and trans-pT231-tau conformations as biomarkers for AD diagnosis, it is important to produce monoclonal antibodies that distinguish cis- and trans-pT231-Pro motif in tau. We immunize rabbits with pT231-Prx tau peptide (KVAVVR-(pT231)-(Prx)-PKSPS; SEQ ID NO: 5) and screen hybridoma clones producing antibodies recognizing pT231-tau in the cis or trans conformation using various in vitro and in vivo procedures known to one of skill in the art.

Example 7

Levels of Cis- and Trans-pT231-tau in Brain Tissue and CSF at Different Stages of AD Human AD brain tissue samples and normal controls are obtained from brain autopsy and ventricular CSF samples collected from the patients with Braak I-VI stage disease. The levels of cis- and trans-pT231-tau in CSF samples are measured using INNOTEST hTau ELISA kit (Innogenetics), replacing the detection antibody with cis- and trans-pT231-tau polyclonal antibodies or mAb. A pT231-tau synthetic peptide is used as a standard. Simultaneous measurement of t-tau, pT231-tau, and $A\beta 1$-42 in CSF has been well established using the multiplex xMAP Luminex platform with Innogenetics' immunoassay kit-based reagents (INNO-BIA AlzBio3; Ghent, Belgium). Alternatively, it is possible to replace the pT231 detection antibody CP9 with cis- and trans-specific antibodies to simultaneously measure cis- and trans-pT231-tau levels with t-tau and $A\beta 1$-42. Calibration curves are produced for each biomarker using aqueous buffered solutions that contain the combination of three biomarkers at different concentrations of recombinant tau, synthetic $A\beta 1$-42 peptide, and pT231-tau synthetic peptide as standards. Assays are carried out in triplicate for each sample and the OD values imported into SPSS analytical software and transformed into concentrations according to the standard curve for statistical analysis.

To understand the relationship between pT231-tau conformations in CSF and in brain tissue, ELISA is used to quantify cis- and trans-pT231-tau levels in brain lysates Immunostaining and immunoblotting analyses are performed on frontal cortex tissues from the same individuals whose CSF samples are analyzed to confirm the ELISA results. To examine the relationship between pT231-tau conformations and other tau-related pathologies, the relationship between cis- and trans-pT231-tau and the presence of the pretangle pathology and/or neurofibrillary lesion is determined. The pre-tangle pathology is detected by immunostaining brain sections with various phospho-specific and/or conformation-specific tau antibodies or by extracting tau from brains using sarcosyl, followed by immunoblotting analysis with various tau antibodies. The presence of neurofibrillary lesions and neurodegeneration is detected by Gallyas silver staining, thioflavin-S staining, NeuN staining, and Nissl staining. To compare the changes of tau conformations and their relationship with other tauopathy phenotypes at different Braak stages, immunoblotting data is quantified with imagequant or immunofluoresence staining, using Zeiss LSM510 META imaging system and software for statistically relevant analysis. A comparative study of cis- and trans-pT231-tau, pT231-tau, total tau, and $A\beta 1$-42 levels at various Braak stages, among AD and other different dementia groups, or among other quantitative measures of AD progression (such as age-at-onset (AAO), disease duration, and Mini-Mental State Examination (MMSE) score) is completed by using Student t test or by one-way analysis of variance followed by Bonferroni post hoc test when multiple comparisons are performed. All data analyses are performed with statistical software.

Example 8

Developing Cis pT231-tau Peptide-based Vaccines for Active Immunotherapy

Two cis pT231-tau peptides are synthesized: 1) KVAVVR-(pT231)-(Dmp)-PKSPS (SEQ ID NO: 1) and 2) KKVAVVR-(pT231)-(Thz)-PKSPS (SEQ ID NO: 2) which we found to be 96% and 100% in the cis conformation, respectively. Wild-type KVAVVR-(pT231)-(Pro)-PKSPS (SEQ ID NO: 4), having 10% in the cis conformation, is used as a control. To examine the immunogenicity of these pT231-tau peptides in generating conformation specific antibodies, non-transgenic pure B6 mice are used in initial testing. Briefly, pT231-tau peptides are mixed overnight at 4° C. with Adju-Phos adjuvant (Brenntag Biosector, Denmark) at 1 mg/ml and then injected s.c. 100 µl into 1-2 month old of mice, followed by a second injection 2 weeks later and then monthly thereafter for several months. Production of conformation-specific pT231-tau antibodies and possibly tau autoantibodies in the serum and brain of mice is measured biweekly after immunization using ELISA and, if needed immunostaining.

The effects of the immunization on the following neurological symptoms, neuropathology and cognitive function in tauopathy mice is measured.

1) Effects on neurological symptoms. All animals are examined daily for the appearance of neurological symptoms, which are scored from 0-6, 0, no clinical signs; 1, tail weakness; 2, hind limb weakness sufficient to impair righting; 3, one limb plegic; 4, paraplegia with forelimb weakness; 5, quadriplegia; and 6, death, as described.

2) Effects on tau conformations, tau-related pathologies and neurodegeneration.

At the end of immunotherapy, immunocytochemistry and immunofluorescence staining is performed 1) to determine the changes in levels and localization of cis and trans p-tau conformations, 2) to determine the presence of the pretangle pathology, detected by various phospho- and/or conformation-specific tau antibodies, or neurofibrillary lesions and neurodegeneration by Gallyas silver staining, thioflavin-S staining, NeuN staining, Nissl staining and if needed, electron microscopy Immunoblotting analysis or quantitative ELISA assays can be performed on selected samples in various neuronal compartments, including sarcosylsoluble and -insoluble, NFT- and non-NFT-associated fractions to determine the relationship between cis and trans p-tau and other tau pathologies. Further, quantitative ELISA assay, quantify immunoblots using imagequant, and/or immunostaining using a Zeiss LSM510 imaging system for statistically relevant analysis can also be performed.

3) Effects on Memory Deficits.

Although human tau transgenic mice do not fully recapitulate all the pathology observed in AD patients, they do demonstrate tau-associated neurodegeneration and significant learning and memory impairments. Tau transgenic mice, including htau mice display tau hyperphosphorylation, impaired place learning and memory before NFTs, even though some of them do not form NFTs nor display neuronal loss. These results suggest that the accumulation of hyperphosphorylated tau that occurs before NFT formation has a major effect on cognitive functions. Notably, in 3 repeat human WT tau transgenic mice, the immunoreactivity of cis pT231 tau was primarily found in the cerebral cortex and the hippocampus, two brain regions critically involved in learning and memory processes. Moreover, it has been reported that T231/Ser235 phosphorylation significantly increases in the hippocampus of mice undergoing contextual fear conditioning and pT231-tau levels might affect cognitive function. Finally, immunization against Pro-directed phosphorylation sites in tau, including pT231, has been shown to improve memory deficits in mice, including htau mice. Thus, cis pT231-tau immunization can improve memory deficit in tauopathy mice.

Since htau mice or P301L mice show age-dependent cognitive impairments and Pin1-KO mice display age-dependent tauopathy, a cross-sectional study to characterize both 6-9 and 15-20 months for Pin1-KO mice, or 4 and 12 months for htau mice or P301L mice, with 12-15 mice in each group, can be performed. The following test battery can be used to assess multiple aspects of cognitive functions (i.e., attention, recognition memory, working memory, procedural learning and memory, visual discrimination learning, fear memory, executive functions), as well as other psychiatric and neurological functions (i.e., muscle tone, motor coordination, anxiety, sociability, exploratory activity, startle reflex and prepulse inhibition). Methods for each of the tests and data analyses follow standard procedures.

To examine the effects of active immunization on cognitive function and ptau conformations, behavioral changes are correlated with the content and/or subcellular localization of cis or trans pT231 in the above mouse models. To this end, hippocampus and cerebral cortex can be rapidly prepared from mice after completion of the behavioral test battery, and divided into two halves preparing for respective immunostaining, immunoblotting and ELISA analyses using cis and trans antibodies.

OTHER EMBODIMENTS

From the foregoing description, it will be apparent that variations and modifications may be made to the invention described herein to adopt it to various usages and conditions. Such embodiments are also within the scope of the following claims.

All publications, patent applications, and patents mentioned in this specification are herein incorporated by reference to the same extent as if each independent publication, patent application, or patent was specifically and individually indicated to be incorporated by reference.

From the foregoing description, one skilled in the art can easily ascertain the essential characteristics of this invention; can make various changes and modifications of the invention to adapt it to various usages and conditions. Thus, other embodiments are also within the claims.

What is claimed is:

1. A method of vaccinating a human subject at risk of developing a tauopathy or a tau-related disease, said method comprising administering a proline-analog-containing antigenic peptide to said human subject in an amount sufficient to treat said human subject by generating an effective amount of a conformation-specific antibody that specifically binds to a Xaa-Pro motif of a naturally occurring polypeptide to reduce the risk of developing said tauopathy or tau-related disease in said human subject,
   wherein said antigenic peptide comprises a Xaa-Pro motif comprising said proline analog,
   wherein said proline analog is selected from the group consisting of homoproline, azetidine-2-carboxylic acid (Aze), tert-butyl-L-proline (TBP), 2,2-dimethyl-thiazolidine (Thz), and cis-4-fluoro-L-proline (c-4F-Pro), and
   wherein the polypeptide is a peptidyl-prolyl cis/trans isomerase (PPIase) substrate, the Xaa of said antigenic peptide is serine or threonine that is phosphorylated, the peptidyl-prolyl bond of said Xaa-Pro motif of said antigenic peptide is in a cis conformation, and said conformation-specific antibody binds to the cis conformation of said Xaa-Pro motif of said polypeptide with at least 10- to 100-fold greater affinity than to the trans conformation of said Xaa-Pro motif of said polypeptide.

2. The method of claim 1, wherein said PPIase substrate is a Pin1 substrate.

3. The method of claim 2, wherein said Pin1 substrate is NIMA, RAB4, CDC25, WEE1, PLK1, MYT1, CDC27, CENP-F, Incenp, RBP1, NHERF-1, KRMP1, CK2, TopoIIα, DAB2, p54nrb, Sil, EMI1, cyclin D1, Ki67, c-Myc, cyclin E, c-Jun, 62-catenin, Cf-2, NF-κB, RAF1, C-Fos, RARα, AIB1/SRC-3, HBx, STAT3, p53, Bcl-2, p73, BimEL, p66$^{Shc}$, CHE1, tau, amyloid precursor protein (APP), APP fragment, synphilin-1, gephyrin, MCL1, NFAT, AUF1, IRF3, BTK, SIN3-RPD3, or hSpt5.

4. The method of claim 1, wherein said polypeptide is tau or APP.

5. The method of claim 1, wherein said tauopathy or tau-related disease is selected from the group consisting of Alzheimer's disease, frontotemporal dementia with Parkinsonism linked to chromosome 17, Pick's disease, and a corticobasal degeneration.

6. The method of claim 1, wherein said antigenic peptide is at least 8 amino acid residues in length.

7. The method of claim 6, wherein said antigenic peptide is between 8 and 20 amino acid residues in length.

8. The method of claim 1, wherein said antigenic peptide comprises the sequence KKVAVVR-(pT231)-(Thz)-PKSPS (SEQ ID NO: 2).

9. The method of claim 1, wherein said antigenic peptide is administered subcutaneously.

10. The method of claim 1, wherein said administration further comprises administering a booster dose.

11. The method of claim 1, wherein said antigenic peptide is formulated with an immunostimulating adjuvant.

12. The method of claim 1, wherein said tauopathy or tau-related disease is selected from the group consisting of Alzheimer's disease, mild cognitive impairment, Parkinson's disease, multiple sclerosis, muscular dystrophy, corticobasal degeneration, dementia pugilistica, Down's syndrome, frontotemporal dementias, myotonic dystrophy, Niemann-Pick disease, Pick's disease, prion disease, progressive supranuclear palsy, subacute sclerosing panencephalistis, convulsive disorders, vascular dementia, age-related dementia, head trauma, stroke, neurofibromatosis, Lewy body disease, amyotrophic lateral sclerosis, peripheral neuropathies, and macular degeneration.

* * * * *

UNITED STATES PATENT AND TRADEMARK OFFICE
CERTIFICATE OF CORRECTION

PATENT NO. : 10,487,114 B2  
APPLICATION NO. : 14/113991  
DATED : November 26, 2019  
INVENTOR(S) : Kun Ping Lu et al.

Page 1 of 1

It is certified that error appears in the above-identified patent and that said Letters Patent is hereby corrected as shown below:

In the Claims

Column 35, Claim 3, Line 33, replace "62-catenin" with --β-catenin--.

Signed and Sealed this  
Twenty-ninth Day of June, 2021

Drew Hirshfeld  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 5

<210> SEQ ID NO 1
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (8)..(8)
<223> OTHER INFORMATION: Xaa is dimethyl proline

<400> SEQUENCE: 1
```

```
Lys Val Ala Val Val Arg Thr Xaa Pro Lys Ser Pro Ser
1               5                   10
```

<210> SEQ ID NO 2
<211> LENGTH: 14
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (9)..(9)
<223> OTHER INFORMATION: Xaa is 2,2-dimethyl-thiazolidine

<400> SEQUENCE: 2

```
Lys Lys Val Ala Val Val Arg Thr Xaa Pro Lys Ser Pro Ser
1               5                   10
```

<210> SEQ ID NO 3
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 3

```
Val Asp Ala Ala Val Thr Pro Glu Glu Arg His Leu Ser Lys
1               5                   10
```

<210> SEQ ID NO 4
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION

<400> SEQUENCE: 4

```
Lys Val Ala Val Val Arg Thr Pro Pro Lys Ser Pro Ser
1               5                   10
```

<210> SEQ ID NO 5
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (8)..(8)
<223> OTHER INFORMATION: Xaa is any proline analog

<400> SEQUENCE: 5

```
Lys Val Ala Val Val Arg Thr Xaa Pro Lys Ser Pro Ser
1               5                   10
```